(12) United States Patent  
Suzuki et al.

(10) Patent No.: US 7,105,520 B2
(45) Date of Patent: Sep. 12, 2006

(54) PHENYLALANINE DERIVATIVES

(75) Inventors: Nobuyasu Suzuki, Kawasaki (JP); Toshihiko Yoshimura, Kawasaki (JP); Hiroyuki Izawa, Kawasaki (JP); Shingo Makino, Kawasaki (JP); Eiji Nakanishi, Kawasaki (JP); Masahiro Murata, Kawasaki (JP); Takashi Tsuji, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 471 days.

(21) Appl. No.: 10/252,003

(22) Filed: Sep. 23, 2002

(65) Prior Publication Data

US 2003/0130320 A1    Jul. 10, 2003

Related U.S. Application Data

(63) Continuation of application No. PCT/JP01/02257, filed on Mar. 22, 2001.

(30) Foreign Application Priority Data

Mar. 23, 2000  (JP)  ............... 2000-081130

(51) Int. Cl.
C07D 239/30   (2006.01)
A61K 31/505   (2006.01)
A61P 9/00     (2006.01)
A61P 11/06    (2006.01)
A61P 35/00    (2006.01)

(52) U.S. Cl. ............... 514/252.14; 544/242; 544/316; 544/318; 544/333; 514/269; 514/274; 514/256

(58) Field of Classification Search ............ 544/242, 544/316, 318, 333; 514/252.14, 269, 274, 514/256
See application file for complete search history.

(56) References Cited

FOREIGN PATENT DOCUMENTS

| WO | 98/44797 | 10/1998 |
|---|---|---|
| WO | 99/10312 | 3/1999 |
| WO | 99/10313 | 3/1999 |
| WO | 99/26923 | 6/1999 |
| WO | 99/37618 | 7/1999 |
| WO | 99/43642 | 9/1999 |
| WO | 99/64390 | 12/1999 |
| WO | 00/37429 | 6/2000 |
| WO | 00/48994 | 8/2000 |

OTHER PUBLICATIONS

U.S. Appl. No. 10/183,729, filed Jun. 28, 2002, Tanaka et al.
U.S. Appl. No. 10/150,067, filed May 20, 2002, Tanaka et al.
U.S. Appl. No. 10/300,856, filed Nov. 21, 2002, Makino et al.
U.S. Appl. No. 10/402,006, filed Mar. 31, 2003, Suzuki et al.
U.S. Appl. No. 10/866,260, filed Jun. 14, 2004, Okuzumi et al.
U.S. Appl. No. 10/921,929, filed Aug. 20, 2004, Sagi et al.

Angela Zeidler et al, "Therapeutic Effects of Antibodies Against Adhesion Molecules in Murine Collagen Type II-Induced Arthritis", *Autoimmunity*, 1995, vol. 21, pp. 245-252.

Daniel K. Podolsky et al, "Attenuation of Colitis in the Cotton-top Tamarin by Anti-α4 integrin Monoclonal Antibody". *J. Clin. Invest.*, Jul. 1993, vol. 92, pp. 372-380.

Tsutomu Takeuchi et al, "Upregulated Expression and Function of Integrin Adhesive Receptors in Systemic Lupus Erythematosus Patients with Vasculitis", *J. Clin. Invest.*, Dec. 1993, vol. 92, pp. 3008-3016.

S. M. Wellicome et al, "Detection of a circulating form of vascular cell adhesion molecule-1:raised levels in rheumatoid arthritis and systemic lupus erythematosus", *Clin. Exp. Immunol.*, 1993, vol. 92, pp. 412-418.

Ted A. Yednock et al, "Prevention of experimental autoimmune encephalomyelitis by antibodies against α4β1 integrin", *Nature*, Mar. 5, 1992, vol. 356, pp. 63-66.

Jody L. Baron et al, "Surface Expression of α4 integrin by CD4 T Cells Is Required for Their Entry into Brain Parenchyma", *J. Exp. Med.*, Jan. 1993, vol. 177, pp. 57-68.

Ichiro Saito et al, "Expression of Cell Adhesion Molecules in the Salivary and Lacrimal Glands of Sjogren's Syndrome", *Journal of Clinical Laboratory Analysis*, 1993, vol. 7, pp. 180-187.

(Continued)

*Primary Examiner*—Kahsay Habte
(74) *Attorney, Agent, or Firm*—Oblon, Spivak, McClelland, Maier & Neustadt, P.C.

(57) ABSTRACT

Phenylalanine derivatives of the following formulae and analogues thereof have an antagonistic activity to α4 integrin. They are used as therapeutic agents for various diseases concerning α4 integrin

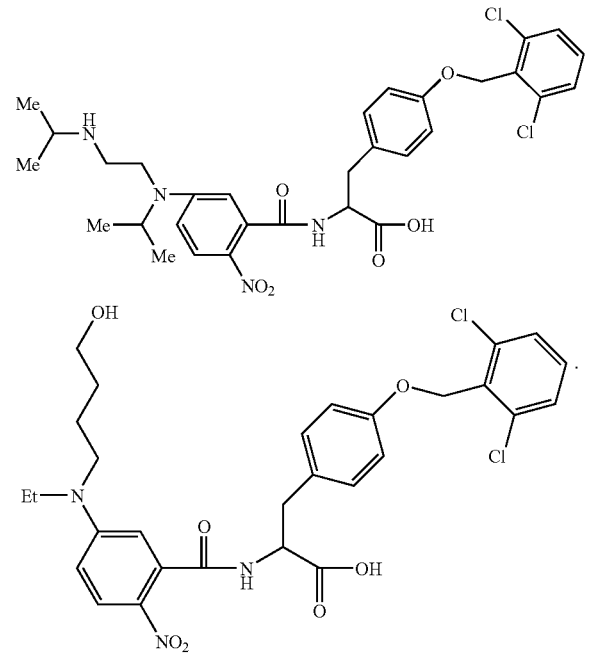

8 Claims, No Drawings

OTHER PUBLICATIONS

William M. Abraham et al, "α₄-Integrins Mediate Antigen-Induced Late Bronchial Responses and Prolonged Airway Hyperresponsiveness in Sheep", *J. Clin. Invest.*, Feb. 1994, vol. 93, pp. 776-787.

Hironori Sagara et al, "A Monoclonal Antibody against Very Late Activation Antigen-4 Inhibits Eosinophil Accumulation and Late Asthmatic Response in a Guinea Pig Model of Asthma", *Int. Arch. Allergy Immunol.*, 1997, vol. 112, pp. 287-294.

Sumi Onuma, "Immunohistochemical Studies of Infiltrating Cells in Early and Chronic Lesions of Psoriasis", *The Journal of Dermatology*, 1994, vol. 21, pp. 223-232.

Toshinori Matsui et al, "Effects of anti-VLA-4 Monoclonal Antibody Treatment in Murine Model of Allergic Rhinitis", *Acta Otolaryngol.*, 2000, vol. 120, pp. 761-765.

Nobuyuki Ebihara et al, "Anti VLA-4 monoclonal antibody inhibits eosinophil infiltration in allergic conjunctivitis model of guinea pig", *Current Eye Research*, 1999, vol. 19, No. 1, pp. 20-25.

Jody L. Baron et al, "The Pathogenesis of Adoptive Murine Autoimmune Diabetes Requires and interaction between α4-Integrins and Vascular Cell Adhesion Molecule-1", *J. Clin. Invest.*, Apr. 1994, vol. 93, pp. 1700-1708.

Simcha R. Meisel et al, "Increased Expression of Neutrophil and Monocyte Adhesion Molecules LFA-1 and Mac-1 and Their Ligand ICAM-1 and VLA-4 Throughout the Acute Phase of Myocardial Infarction", *JACC*, Jan. 1998, vol. 31, No. 1, pp. 120-125.

Peggy T. Shih et al, "Blocking Very Late Antigen-4 Integrin Decreases Leukocyte Entry and Fatty Streak Formation in Mice Fed an Atherogenic Diet", *Circ. Res.*, Feb. 19, 1999, vol. 84, pp. 345-351.

Alan B. Lumsden et al, "Anti-VLA-4 antibody reduces intimal hyperplasia in the endarterectomized carotid artery in nonhuman primates", *Journal of Vascular Surgery*, Jul. 1997, vol. 26, No. 1, pp. 87-93.

Yoshihisa Mori et al, "Anti-α4 integrin antibody suppresses the development of multiple myeloma and associated osteoclastic osteolysis", *Blood*, Oct. 1, 2004, vol. 104, No. 7, pp. 2149-2154.

Hitoshi Okahara et al, "Involvement of Very Late Activation Antigen 4 (VLA-4) and Vascular Cell Adhesion Molecule 1 (VCAM-1) in Tumor Necrosis Factor α Enhancement of Experimental Metastasis", *Cancer Research*, Jun. 15, 1994, vol. 54, pp. 3233-3236.

Mitsuaki Isobe et al, "Immunosuppression to Cardiac Allografts and Soluble Antigens by Anti-Vascular Cellular Adhesion Molecule-1 and Anti-Very Late Antigen-4 Monoclonal Antibodies", *The Journal of Immunology*, 1994, vol. 153, pp. 5810-5818.

Yoji Shimizu et al, "Integrins in the Immune System," *Advances in Immunology*, 1999, vol. 72, pp. 325-380.

PHENYLALANINE DERIVATIVES

CROSS REFERENCES TO RELATED APPLICATIONS

This application is a continuation of International Patent Application No. PCT/JP01/02257, filed on Mar. 22, 2001, and claims priority to Japanese Patent Application No. 2000-081130, filed on Mar. 23, 2000.

BACKGROUND OF THE INVENTION

The present invention relates to new phenylalanine derivatives and the use of the phenylalanine derivatives as medicines. It was reported that α 4 integrins participate in diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α 4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the reparation of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β 1 through β 8 subfamilies) depending on the β chains thereof. Known typical subfamilies are β 1 and β 3 subfamilies involved in the adhesion of cell ingredients to the extracellular matrixes such as collagen and fibronectin; β 2 subfamily involved in cell-to-cell adhesion in the immune system; and β 7 subfamily which mainly participates in the infiltration of leukocytes into mucosal tissues (Shimizu et al., Adv. Immunol. 72: 325–380, 1999). As for the above-described α 4 integrins, two kinds of molecules thereof are known. They are VLA-4 (very late antigen-4) molecule belonging to the β 1 subfamily and comprising α 4β1 chain and LPAM-1 (lymphocyte Peyer's patch HEV adhesion molecule-1) molecule belonging to the β 7 subfamily and comprising α 4β7 chain. Usually most of leukocytes circulating in the blood have only a low adhesion affinity for the vascular-endothelium cells and they cannot move out of the blood vessel. On the other hand, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymph vessel under the physiological conditions. It is known that LPAM-1 molecules participate in the lymphocyte homing into the lymphoid tissue of an intestinal tract such as Peyer's patch (Butcher et al., Adv. Immunol. 72: 209–253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325–380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrixes is also known (Shimizu et al., Adv. Immunol. 72: 325–380, 1999). The β 1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β3 subfamily and β 5 subfamily, recognize arginine—glycine—aspartic acid (RGD) sequence in fibronectin, vitronectin, tenascin and osteopontin. On the other hand, in the interaction of VLA-4 and fibronectin, the RGD sequence does not participate but a CS1 peptide fragment comprising leucine—aspartic acid—valine (LDV) as the core sequence participates (Pulido et al., J. Biol. Chem. 266: 10241–10245, 1991). Clements et al. found a sequence similar to LDV in amino acid sequences of VCAM-1 and MAdCAM-1. It has been elucidated that a mutant obtained by partially modifying the CS-1-like sequence of VCAM-1 and MAdCAM-1 molecules cannot interact with VLA-4 or LPAM-1 (Clements et al., J. Cell Sci. 107: 2127–2135, 1994, Vonderheide et al., J. Cell. Biol. 125: 215–222, 1994, Renz et al., J. Cell. Biol. 125: 1395–1406, 1994, and Kilger et al., Int. Immunol. 9: 219–226, 1997). Thus, it was found that the CS-1-like sequence is important for the interaction of VLA-4/LPAM-1 and VCAM-1/MAdCAM-1.

It was reported that the cyclic peptide having the CS-1-like structure is antagonistic to the interaction of VLA-4 or LPAM-1 with VCAM-1, MAdCAM-1 or CS-1 peptide (Vanderslice et al., J. Immunol. 158: 1710–1718, 1997). The above-described facts indicate that all the interaction of α 4 integrin and VCAM-1, MAdCAM-1 or fibronectin can be blocked by using a suitable α 4 integrin antagonist (the term "α 4 integrin antagonist" herein indicates a substance antagonistic to α 4β1 and/or α 4β7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577–584, 1990, Osborn et al., Cell 59: 1203–1211, 1989 and Issekutz et al., J. Eex. Med. 183: 2175–2184, 1996). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207–4210, 1991 and Morales-Ducret et al., J. Immunol. 149: 1424–1431, 1992), lungs and respiratory tract epithelium in asthma (ten Hacken et al., Clin. Exp. Allergy 12: 1518–1525, 1998) and allergic diseases (Randolph et al., J. Clin. Invest. 104: 1021–1029, 1999), systemic erythematodes (Takeuchi et al., J. Clin. Invest. 92: 3008–3016, 1993), Sjogren's syndrome (Edwards et al., Ann. Rheum. Dis. 52: 806–811, 1993), multiple sclerosis (Steffen et al., Am. J. Pathol. 145: 189–201, 1994) and psoriasis (Groves et al., J. Am. Acad. Dermatol. 29: 67–72, 1993); atherosclerotic plagues (O'Brien et al., J. Clin. Invest. 92: 945–951, 1993), intestinal tissues of the patients with inflammatory bowel diseases such as Crohn's disease and ulcerative colitis (Koizumi et al., Gastroenterol. 103: 840–847, 1992 and Nakamura et al., Lab. Invest. 69: 77–85, 1993), inflamed tissue of Langerhans island of patients with diabetes (Martin et al., J. Autoimmun. 9: 637–643, 1996) and implants during the rejection of transplantation of heart or kidney (Herskowitz et al. Am. J. Pathol. 145: 1082–1094, 1994 and Hill et al., Kidney Int. 47: 1383–1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α 4-integrins was effective in reducing the incidence rate or in reducing encephalomyelitis in the experimental autoimmune encephalomyelitis models, i.e. multiple sclerosis models (Yednock et al., Nature 356: 63–66, 1992 and Baron et al., J. Exp. Med. 177: 57–68, 1993). Zeider et al. reported that in vivo administration of an antibody against α 4-integrin was effective in reducing the incidence rate of mouse collagen arthritis (rheumatism models) (Zeidler et al., Autoimmunity 21: 245–252, 1995). The therapeutic effect of an antibody against α 4-integrin in asthma models was reported by Abraham et al. and Sagara et al. (Abraham et al., J. Clin. Invest. 93: 776–787, 1994 and Sagara et al., Int. Arch. Allergy Immunol. 112: 287–294, 1997). The effect of an antibody against α 4-integrin in inflammatory bowel disease models was reported by Podolsky et al. (Podolsky et al., J. Clin. Invest. 92: 372–380, 1993). The effect of an antibody against α4-integrin and that against VCAM antibody in insulin-dependent diabetes models were reported by Baron et al. (Baron et al., J. Clin. Invest. 93: 1700–1708, 1994). It was made apparent with Baboon models that the restenosis of a blood vessel after an angioplasty carried out because of arteriosclerosis can be inhibited by the administration of α 4 integrin antibody (Lumsden et al., J. Vasc. Surg. 26: 87–93, 1997). It was also reported that α 4 integrin or VCAM antibody is effective in inhibiting the rejection of an implant or inhibiting metastasis of a cancer (Isobe et al., J. Immunol. 153: 5810–5818, 1994 and Okahara et al., Cancer Res. 54: 3233–3236, 1994).

As described above, unlike VCAM-1, MAdCAM-1 which is a ligand of LPAM-1 is constantly expressed on high endothelial venules (HEV) in the intestinal mucous membrane, mesenteric lymph nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97–110, 1997). Hanninen et al. reported that induction of the expression is observed in an inflamed tissue of Langerhans island which is a model of an insulin-dependent diabetes (Hanninen et al., J. Immunol. 160: 6018–6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099–2106, 1997) and the above-described NOD mouse models are improved by the in vivo administration of antibody to MAdCAM or antibody to β-7 integrin (Hanninen et al., J. Immunol. 160: 6018–6025, 1998 and Yang et al., Diabetes 46: 1542–1547, 1997).

The above-described facts indicate the possibility of employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10313 and WO 99/36393. However, none of them is practically used for the therapeutic treatment at present because of poor oral absorption and immunogenic properties during the use of them for a long period of time.

DISCLOSURE OF THE INVENTION

An object of the present invention is to provide new compounds having α4 integrin antagonistic effect.

Another object of the present invention is to provide a pharmaceutical composition containing such a new compound having the α 4 integrin antagonistic effect.

Still another object of the present invention is to provide an α 4 integrin antagonist.

A further object of the present invention is to provide a therapeutic agent or preventive agent for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

After synthesizing various phenylalanine derivatives and examining α 4 integrin antagonistic activities thereof for the purpose of solving the above-described problems, the inventors have found that specified, new phenylalanine derivatives, particularly compounds of the following general formula (1) wherein W represents a group of general formula (3) or general formula (4), have an excellent α 4 integrin antagonistic activity. The present invention has been completed on the basis of this finding.

Namely, the present invention provides phenylalanine derivatives of the following general formula (1) and pharmaceutically acceptable salts thereof:

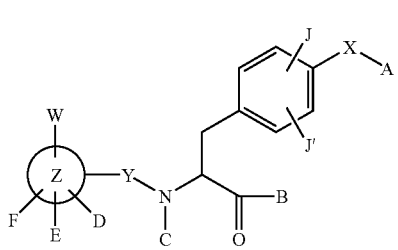

(1)

wherein X represents —O—, —O—SO$_2$—, —NR$^1$—, —NR$^1$—(=O)—, —NR$^1$—SO$_2$—, —NR$^1$—C(=O)—NH—, —NR$^1$—C(=S)—NH— or —C(=O)— wherein R$^1$ represents hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), Y represents —C(=O)—, —C(=S)—, —SO$_2$—, —CH$_2$—(C=O)—, —NH—(C=O)—, —NH—C(=S)— or —CH=CH—(C=O)—

Z represents an aryl group or a heteroaryl group,

A represents a group of the following general formula (2), a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with a group of general formula (2), a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s):

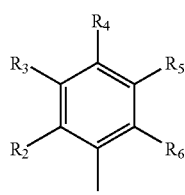

(2)

wherein R$^2$, R$^3$, R$^4$, R$^5$ and R$^6$ may be the same or different from one another, and each represent hydrogen atom, a halogen atom, hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, B represents hydroxyl group, a lower alkoxyl group or hydroxyamino group, C represents hydrogen atom, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a lower alkyl group substituted with a cycloalkyl group(s) which may contain a hetero atom(s) in the ring thereof, a lower alkyl group substituted with an aryl group(s), a lower alkyl group substituted with a heteroaryl group(s), D, E and F may be the same or different from one another, and each represent hydrogen atom, nitro group, a halogen atom, hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, cyano group, a substituted or unsubstituted amino group, carboxyl group, a lower alkoxycarbonyl group, a substituted or unsubstituted carbamoyl group, a lower alkylthio group, a lower alkylsulfonyl group or a substituted or unsubstituted sulfamoyl group, W represents a group of the following general formula (3), (4) or (5):

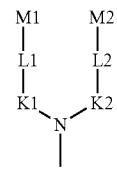

(3)

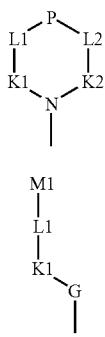

(4)

(5)

wherein:
G represents oxygen atom, sulfur atom, an interatomic bond, —C(=O)—, —C(=S)—SO$_2$— or —S(=O)—, K$^1$ and K$^2$ may be the same or different from each other, and each represent an interatomic bond, —C(=O)—, —C(=S)—SO$_2$— or —S(=O)—, L$^1$ and L$^2$ may be the same or different from each other, and each represent an interatomic bond, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group or a hydroxy-lower alkyl group, M$^1$ and M$^2$ may be the same or different from each other, and each represent hydrogen atom, hydroxyl group, mercapto group, unsubstituted amino group, a monosubstituted amino group, a disubstituted amino group, carboxyl group, sulfo group, sulfino group, sulfeno group, a substituted or unsubstituted carbamoyl group, a substituted or unsubstituted sulfamoyl group, a lower alkyloxy group, a lower alkylthio group, a lower alkoxycarbonyl group, sulfonyl group, sulfinyl group, a halogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, a halogeno-lower alkanoyl group, an aroyl group, nitro group or cyano group, P represents a substituted or unsubstituted lower alkyl group, a substituted or unsubstituted amino group, oxygen atom, sulfur atom, an interatomic bond, —C(=O)— or —CH(OH)—, and J and J' may be the same or different from each other and each represent hydrogen atom, a halogen atom, a lower alkyl group, a lower alkyloxy group or nitro group.

The present invention provides an α 4 integrin antagonist containing the above-described phenylalanine derivative or a pharmaceutically acceptable salt thereof as the active ingredient.

The present invention also provides a therapeutic agent or preventive agent, containing the phenylalanine derivative or a pharmaceutically acceptable salt thereof as the active ingredient, for diseases in which α 4 integrin-depending adhesion process participates in the pathology, such as inflammatory diseases, rheumatoid arthritis, inflammatory bowel diseases, systemic lupus erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group indicates that the group has 1 to 6 carbon atoms in this specification.

Alkyl groups per se and also alkyl groups in alkenyl groups, alkynyl groups, alkoxyl groups, alkylthio groups, alkanoyl groups and alkylamino groups, alkenyl groups and alkynyl groups may be either linear or branched.

The alkyl groups are preferably those having 1 to 6 carbon atoms, such as methyl group, ethyl group, propyl group, isopropyl group, butyl group, secondary butyl group, tertiary butyl group, pentyl group and hexyl group.

The alkenyl groups are preferably those having 2 to 6 carbon atoms, such as vinyl group, propenyl group, butenyl group and pentenyl group.

The alkynyl groups are preferably those having 2 to 6 carbon atoms, such as ethynyl group, propynyl group and butynyl group.

The cycloalkyl groups are preferably those having 3 to 10 carbon atoms, such as cyclopropyl group, cyclobutyl group, cyclopentyl group, cyclohexyl group, norbornyl group, adamantyl group and cyclohexenyl group.

The alkoxyl groups are preferably those having 1 to 6 carbon atoms, such as methoxyl group, ethoxyl group, propyloxy group and isopropyloxy group.

The hetero atoms include nitrogen, oxygen, sulfur, etc.

The halogen atoms are fluorine atom, chlorine atom, bromine atom and iodine atom.

The halogenoalkyl groups include chloromethyl group, trichloromethyl group, trifluoromethyl group, trifluoroethyl group, pentafluoroethyl group, etc.

The halogenoalkoxyl groups include trichloromethoxyl group, trifluoromethoxyl group, etc.

The hydroxyalkyl groups include hydroxymethyl group, hydroxyethyl group, etc.

Examples of the cycloalkyl groups which may contain a hetero atom(s) in the ring thereof include piperidyl group, piperazinyl group, morpholinyl group, pyrrolidinyl group and tetrahydrofuranyl group.

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups and halogenoalkoxyl groups.

The aryl groups in Z are unsubstituted aryl groups such as phenyl group, 1-naphthyl group and 2-naphthyl group. Phenyl group is particularly preferred.

The heteroaryl groups are both substituted and unsubstituted heteroaryl groups such as pyridyl group, pyrimidyl group, furyl group, thienyl group, indolyl group, quinolyl group and isoquinolyl group. Preferred heteroaryl groups are pyridyl group, furyl group, thienyl group and substituted pyridyl groups, substituted furyl groups and substituted thienyl groups. Particularly preferred substituents are halogen atoms, alkoxyl groups, alkyl groups, hydroxyl group, halogenoalkyl groups and halogenoalkoxyl groups.

The heteroaryl groups in Z are unsubstituted heteroaryl groups such as pyridyl group, pyrimidyl group, furyl group, thienyl group, indolyl group, quinolyl group and isoquinolyl group. Pyridyl group, furyl group and thienyl group are preferred.

The lower alkyl groups substituted with an aryl group include, for example, benzyl group and substituted benzyl groups. Particularly preferred substituents are halogen atoms, alkoxyl groups, alkyl groups, hydroxyl group, halogenoalkyl groups and halogenoalkoxyl groups.

The lower alkyl groups substituted with a heteroaryl group include, for example, pyridylmethyl group, and particularly preferred substituents thereof are halogen atoms, alkoxyl groups, alkyl groups, hydroxyl group, halogenoalkyl groups and halogenoalkoxyl groups.

The alkanoyl groups are preferably those having 1 to 6 carbon atoms, such as formyl groups, acetyl groups, propanoyl group, butanoyl group and pivaloyl group.

The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups.

The halogenoalkanoyl groups include, for example, trichloroacetyl group and trifluoroacetyl group.

The alkylsulfonyl groups include, for example, methanesulfonyl group and ethanesulfonyl group.

The arylsulfonyl groups include, for example, benzenesulfonyl group and p-toluenesulfonyl group.

The heteroarylsulfonyl groups include, for example, pyridylsulfonyl group.

The halogenoalkylsulfonyl groups include, for example, trifluoromethanesulfonyl group.

The alkyloxycarbonyl groups include, for example, methoxycarbonyl group, ethoxycarbonyl group and tert-butoxycarbonyl group.

The aryl-substituted alkoxycarbonyl groups include, for example, benzyloxycarbonyl group and 9-fluorenylmethoxycarbonyl group.

The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups.

The substituted thiocarbamoyl groups include, for example, methylthiocarbamoyl group, phenylthiocarbamoyl group and substituted phenylthiocarbamoyl groups, and the substituents thereof are particularly preferably halogen atoms, alkoxyl groups, alkyl groups, hydroxyl group, halogenoalkyl groups and halogenoalkoxyl groups.

The substituted sulfamoyl groups include, for example, N-methylsulfamoyl group and N-methyl(thiosulfamoyl) group. N-methylsulfamoyl group is particularly preferred as the substituent.

The substituents in the substituted amino groups herein include lower alkyl groups, lower alkyl groups substituted with an aryl group, lower alkyl groups substituted with a heteroaryl group, lower alkanoyl groups, aroyl groups, halogeno-lower alkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups.

The monosubstituted amino groups in $M^1$ and $M^2$ are preferably those having 1 to 6 carbon atoms, such as methylamino group, ethylamino group, n-propylamino group, isopropylamino group and phenylamino group. Particularly preferred groups are ethylamino group, isopropylamino group and n-propylamino group.

The disubstituted amino groups in $M^1$ and $M^2$ are preferably those having 2 to 12 carbon atoms, such as dimethylamino group, diethylamino group, diisopropylamino group, methyl-n-propylamino group and diphenylamino group. Dimethylamino group is particularly preferred.

The groups represented by general formula (3) are those composed of preferred groups of $K^1$, $K^2$, $L^1$, $L^2$, $M^1$ and $M^2$. In particular, preferred groups are (N-isopropylaminoethyl-N'-isopropyl)amino group, (N-n-propylaminobutyl-N'-n-propyl)amino group, (N-hydroxybutyl-N'-ethyl)amino group, (N-isopropylaminopropyl-N'-isopropylamino) group, (N-ethylaminobutene-2-yl-N'-ethyl)amino group and (N-ethyl amino ethyl-N'-ethyl)amino group. (N-isopropylaminoethyl-N'-isopropyl)amino group, (N-n-propylaminobutyl-N'-n-propyl)amino group and (N-hydroxybutyl-N'-ethyl)amino group are particularly preferred.

The groups represented by general formula (4) are those composed of preferred groups of $K^1$, $K^2$, $L^1$, $L^2$ and P. Concretely, the groups are substituted or unsubstituted piperidyl group, substituted or unsubstituted piperazinyl group, morpholinyl group, pyrrolidinyl group and tetrahydrofuranyl group. Particularly preferred groups are unsubstituted piperidyl group, unsubstituted piperazinyl group, 2,5-dimethylpiperidyl group and 2,5-dimethylpiperadinyl group.

The groups represented by general formula (5) are those composed of preferred groups of G, $K^1$, $L^1$ and $M^1$.

The group represented by X in the above general formula (1) is preferably —O—, —$NR^1$—, —$NR^1$—C(=O)—, —$NR^1$—$SO_2$—, —$NR^1$—C(=O)—NH— or —$NR^1$—C(=S)—NH—. The group represented by X is preferably —O—, —$NR^1$—C(=O)— or —$NR^1$—C(=S)—NH—. —O— or —$NR^1$—C(=O)— is particularly preferred.

$R^1$ is preferably hydrogen atom, a lower alkyl group, a lower alkenyl group, a lower alkynyl group, a lower alkyl group substituted with an aryl group(s), or a lower alkyl group substituted with a heteroaryl group(s).

The group represented by Y is preferably —C(=O)—, —CH=CH—(C=O)—, —$SO_2$—, —NH—(C=O)— or —NH—C(=S)—, —C(=O)— is particularly preferred.

The group represented by Z is preferably an aryl group or a heteroaryl group. It is more preferably an aryl group, particularly phenyl group.

In the groups represented by A, the cycloalkyl groups which may contain a hetero atom(s) in the ring thereof, aryl groups and heteroaryl groups are either substituted or unsubstituted. The substituents thereof are those described above with reference to $R^2$ to $R^6$. The, heteroaryl groups are preferably those having a 5-membered or 6-membered ring having 1 or 2 nitrogen atoms in the ring. Those having 6-membered ring are more preferred. Pyrimidine ring is particularly preferred.

The groups represented by A are particularly preferably lower alkyl groups substituted with a group of general formula (2).

The group represented by B is preferably hydroxyl group or a lower alkoxyl group. Hydroxyl group is particularly preferred.

The group represented by C is preferably hydrogen atom.

The groups represented by D, E and F are particularly hydrogen atom, nitro group, halogen atoms, hydroxyl group, lower alkyl group which may contain a hetero atom(s) in the ring thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a lower alkyloxy group, cyano group, a substituted or unsubstituted amino group, carboxyl group, a lower alkoxycarbonyl group, a substituted or unsubstituted carbamoyl group, a lower alkylthio group or a lower alkylsulfonyl group. Among them, hydrogen atom, amino group and nitro group are preferred. Hydrogen atom and nitro group are particularly preferred. Two or three of the groups represented by D, E and F are preferably hydrogen atoms. It is particularly preferred that two of them are each hydrogen atom.

In the groups represented by D, E and F, the cycloalkyl groups which may contain a hetero atom(s) in the ring thereof, aryl groups and heteroaryl groups are either unsubstituted or substituted, and the substituents are those described above with reference to $R^2$ to $R^6$.

The group represented by W is preferably any of those represented by the above general formula (3), (4) or (5). Those represented by the general formula (3) or (4) are preferred.

The group represented by G is preferably oxygen atom, sulfur atom, an interatomic bond, —C(=O)—, —C(=S)— or —SO$_2$—.

The groups represented by $K^1$ and $K^2$ are each preferably an interatomic bond, —C(=O)—, —C(=S)—SO$_2$— or —S(=O)—. The interatomic bond is particularly preferred.

The groups represented by $L^1$ and $L^2$ are each preferably an interatomic bond, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group or a heteroaryl group. $L^1$ and $L^2$ are each particularly preferably an interatomic bond, a lower alkyl group which may contain a hetero atom(s) in the chain thereof or a lower alkenyl group which may contain a hetero atom(s) in the chain thereof, The groups represented by $M^1$ and $M^2$ are each preferably hydrogen atom, hydroxyl group, mercapto group, unsubstituted amino group, a monosubstituted amino group, a disubstituted amino group, carboxyl group, sulfo group, a substituted or unsubstituted carbamoyl group, a substituted or unsubstituted sulfamoyl group, a lower alkyloxy group, a lower alkylthio group, a lower alkoxycarbonyl group, sulfonyl group, a halogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group(s), a lower alkyl group substituted with a heteroaryl group(s), a lower alkanoyl group, a halogeno-lower alkanoyl group, an aroyl group, nitro group or cyano group. $M^1$ and $M^2$ are each particularly preferably an unsubstituted amino group, a monosubstituted amino group, a disubstituted amino group, hydroxyl group or hydrogen atom.

The group represented by P is preferably a substituted or unsubstituted lower alkyl group, a substituted or unsubstituted amino group, oxygen atom, sulfur atom or an interatomic bond. It is particularly preferably a substituted or unsubstituted lower alkyl group or a substituted or unsubstituted amino group.

The groups represented by J and J' are each particularly preferably hydrogen atom.

It is preferred in the present invention that Z in general formula (1) is phenyl group.

It is preferred that in general formula (1), X is a group of the formula: —O— and A is an alkyl group having one carbon atom and substituted with a group of general formula (2).

It is preferred that in general formula (1), W is a group of general formula (3) or (4), $K^1$ and $K^2$ represent an interatomic bond, $L^1$ and $L^2$ may be the same or different and they each represent a lower alkyl group which may contain a hetero atom(s) in the chain thereof or a lower alkenyl group which may contain a hetero atom(s) in the chain thereof, and $M^1$ and $M^2$ may be the same or different and they each represent hydrogen atom, hydroxyl group, an unsubstituted amino group, a monosubstituted amino group or a disubstituted amino group.

It is preferred that in general formula (1), Z represents phenyl group, D represents nitro group, W represents a group of general formula (3) or general formula (4), $K^1$ and $K^2$ represent an interatomic bond, $L^1$ and $L^2$ may be the same or different from each other and they each represent a lower alkyl group which may contain a hetero atom(s) in the chain thereof or a lower alkenyl group which may contain a hetero atom(s) in the chain thereof, and $M^1$ and $M^2$ may be the same or different and they each represent hydrogen atom, hydroxyl group, an unsubstituted amino group, a monosubstituted amino group or a disubstituted amino group.

It is preferred that in general formula (1), Z represents phenyl group, X represents —O— or —NR1—(C=O)—, A represents an alkyl group having one carbon atom and substituted with a group of general formula (2), D represents nitro group, W represents a group of general formula (3) or general formula (4), $K^1$ and $K^2$ represent an interatomic bond, $L^1$ and $L^2$ may be the same or different from each other and they each represent a lower alkyl group which may contain a hetero atom(s) in the chain thereof or a lower alkenyl group which may contain a hetero atom(s) in the chain thereof, and $M^1$ and $M^2$ may be the same or different and they each represent hydrogen atom, hydroxyl group, an unsubstituted amino group, a monosubstituted amino group or a disubstituted amino group.

It is preferred that in general formula (1), X represents —O— or —NR$^1$—(C=O)—, Y represents a group of the formula: —C(=O)—, Z represents a phenyl group, A represents an alkyl group having one carbon atom and substituted with a group of general formula (2), $R^2$, $R^3$, $R^4$, $R^5$ and $R^6$ may be the same or different from one another and they each represent hydrogen atom or a halogen atom, B represents hydroxyl group, C represents hydrogen atom, D represents nitro group, E and F each represent a hydrogen atom, W represents a group of general formula (3) or general formula (4), $K^1$ and $K^2$ represent an interatomic bond, $L^1$ and $L^2$ may be the same or different from each other and they each represent a lower alkyl group which may contain a hetero atom(s) in the chain thereof or a lower alkenyl group which may contain a hetero atom(s) in the chain thereof, $M^1$ and $M^2$ may be the same or different and they each represent hydrogen atom, hydroxyl group, an unsubstituted amino group, a monosubstituted amino group or a disubstituted amino group, P represents a substituted or unsubstituted lower alkyl group or a substituted or unsubstituted amino group, and J and J' each represent hydrogen atom.

The phenylalanine derivatives (1) of the present invention can be produced by methods described below. In the following general formulae, "●" represents a resin used for the solid phase synthesis, such as Wang resin.

For example, a phenylalanine derivative (8) or (9) of general formula (1) wherein —X-A represents a group defined by Q described below, Y represents a group of the formula: —C(=O)— or —CH=CH—(C=O)—, Z represents phenyl group, B represents hydroxyl group, C represents hydrogen atom, D represents nitro group and E and F each represent hydrogen atom is produced as follows:

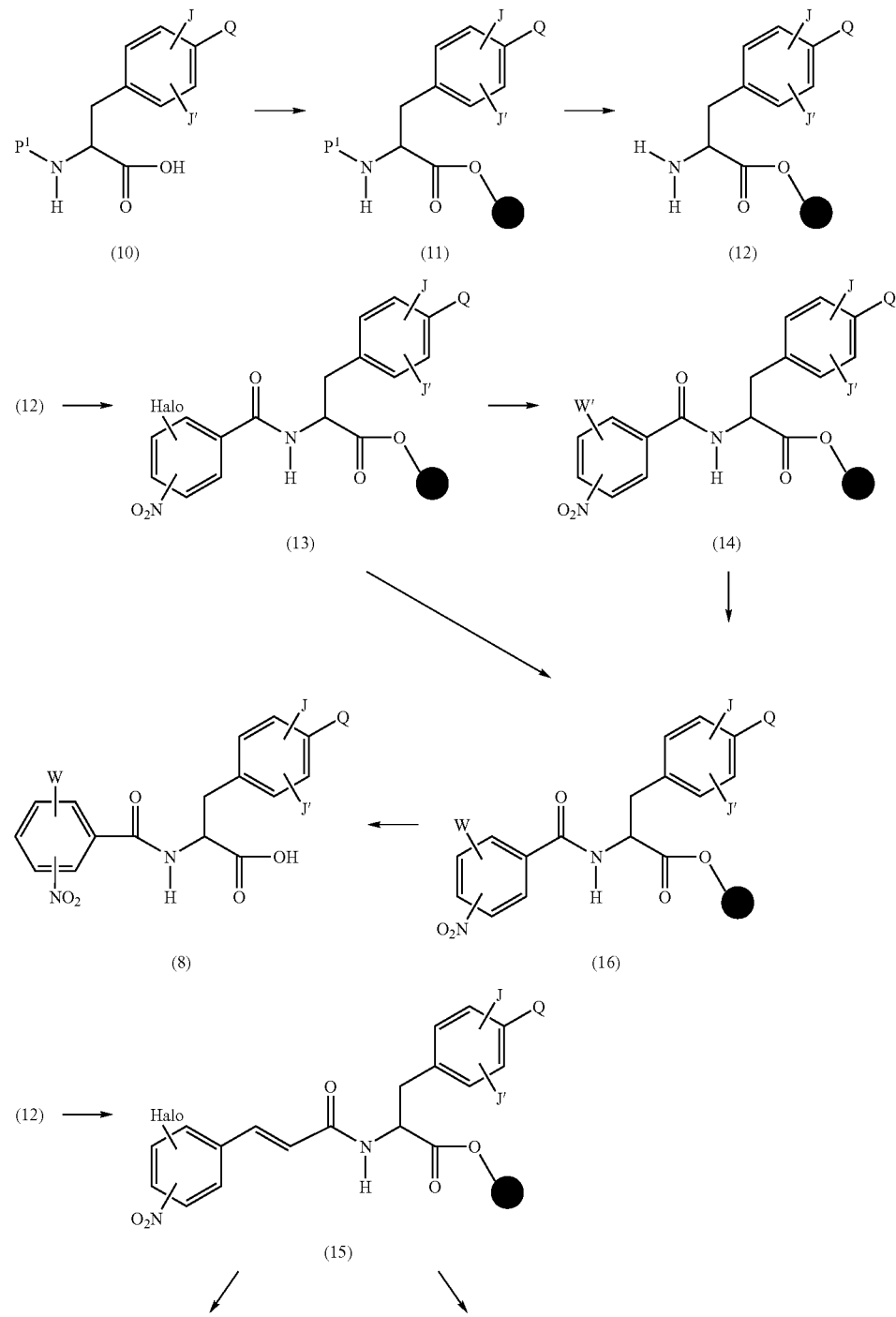

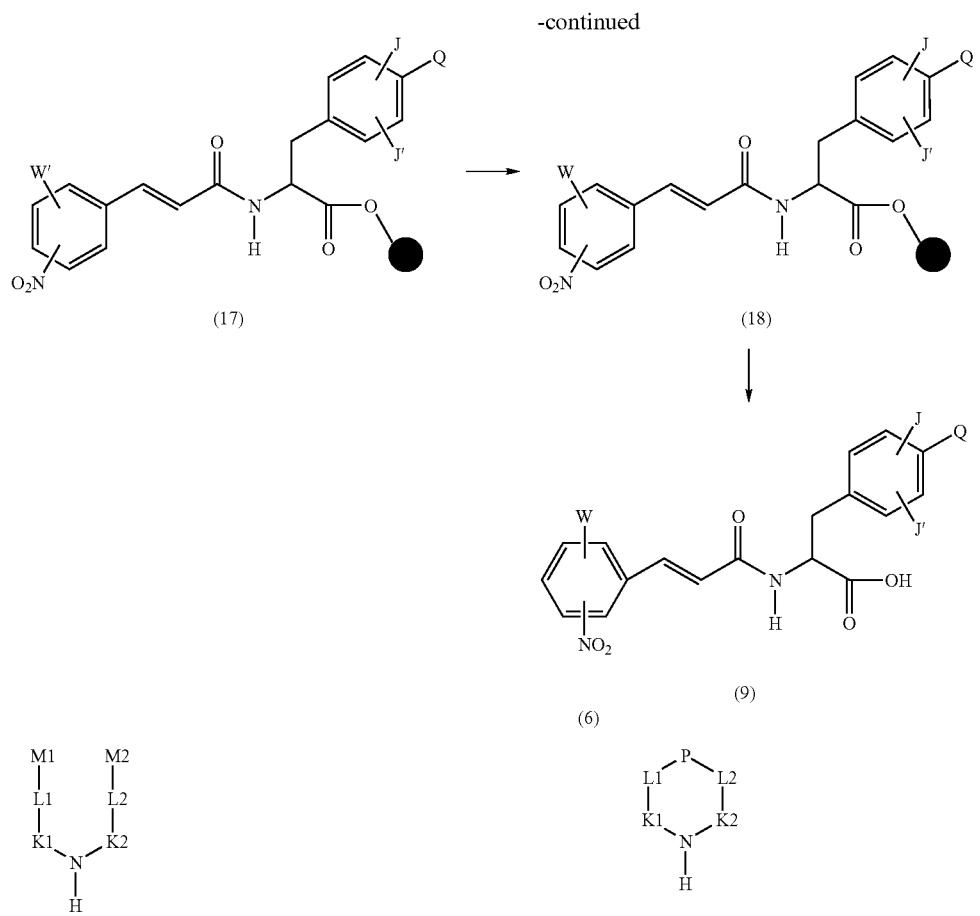

A suitably protected carboxylic acid (10) is introduced into a resin by a usual method. The substituent Q of the carboxylic acid (10) has a structure of —X-A as described above with reference to the general formula (1), it is a substituent convertible into —X-A in any stage of the synthesis or it is suitably protected. As for the introduction reaction conditions, the reaction can be conducted by using, if necessary, a suitable additive such as HOAt (1-hydroxy-7-azabenzotriazole) or HOBt (1-hydroxybenzotriazole) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (11). The protective group $P^1$ is removed from the ester (11) under suitable conditions to obtain an amine (12). For example, when Fmoc group (9-fluorenylmethoxycarbonyl group) is used as $P^1$, the protective group can be removed with a base such as piperidine in a solvent such as DMF. The amine (12) can be converted into an amide (13) or (15) by condensing it with benzoic acid or cinnamic acid substituted with a nitro group and a halogen atom in the presence of a condensing agent such as DIC and, if necessary, a suitable additive such as HOAt or HOBt in an organic solvent such as DMF, NMP or dichloromethane. The amide (13) or (15) can be converted into a phenylamine (16) or (18) by reacting it with an amine (6) or (7) in the presence of, if necessary, a suitable additive such as triethylamine or diisopropylethylamine in an organic solvent such as DMF, NMP, DMSO or dichloromethane. The phenylamine (16) or (18) can be obtained from the amide (13) or (15) through an amide (14) or (17). W' in the amide (14) or (17) represents a group which can be converted into W by removing the protecting group in the following step. The conversion of the amide (13) or (15) into the amide (14) or (17) is conducted under the same conditions as those in the conversion of the amide (13) or (15) into the phenylamine (16) or (18). The obtained amide (14) or (17) can be converted into the phenylamine (16) or (18) by removing the protective group.

The phenylamine (16) or (18) obtained as described above is cut from the resin under suitable conditions to obtain it in the form of a carboxylic acid (8) or (9). For example, when Wang resin is used as the resin, the phenylamine (16) or (18) is treated with an acid reaction solution containing, for example, TFA (trifluoroacetic acid) to obtain a solution of the carboxylic acid (8) or (9) and then the solvent is evaporated to obtain a carboxylic acid (8) or (9). The carboxylic acid (8) or (9) thus obtained is purified by the column chromatography, HPLC, recrystallization or the like to obtain a pure carboxylic acid (8) or (9).

The phenylalanine derivatives (8) or (9) of the general formula (1) wherein —X-A is a group defined by Q given below, Y is a group of —C(=O)— or —CH=CH—(C=O)—, Z is phenyl group, B is hydroxyl group, C is hydrogen atom, D is nitro group and E and F are each hydrogen atom can be synthesized also by the following method:
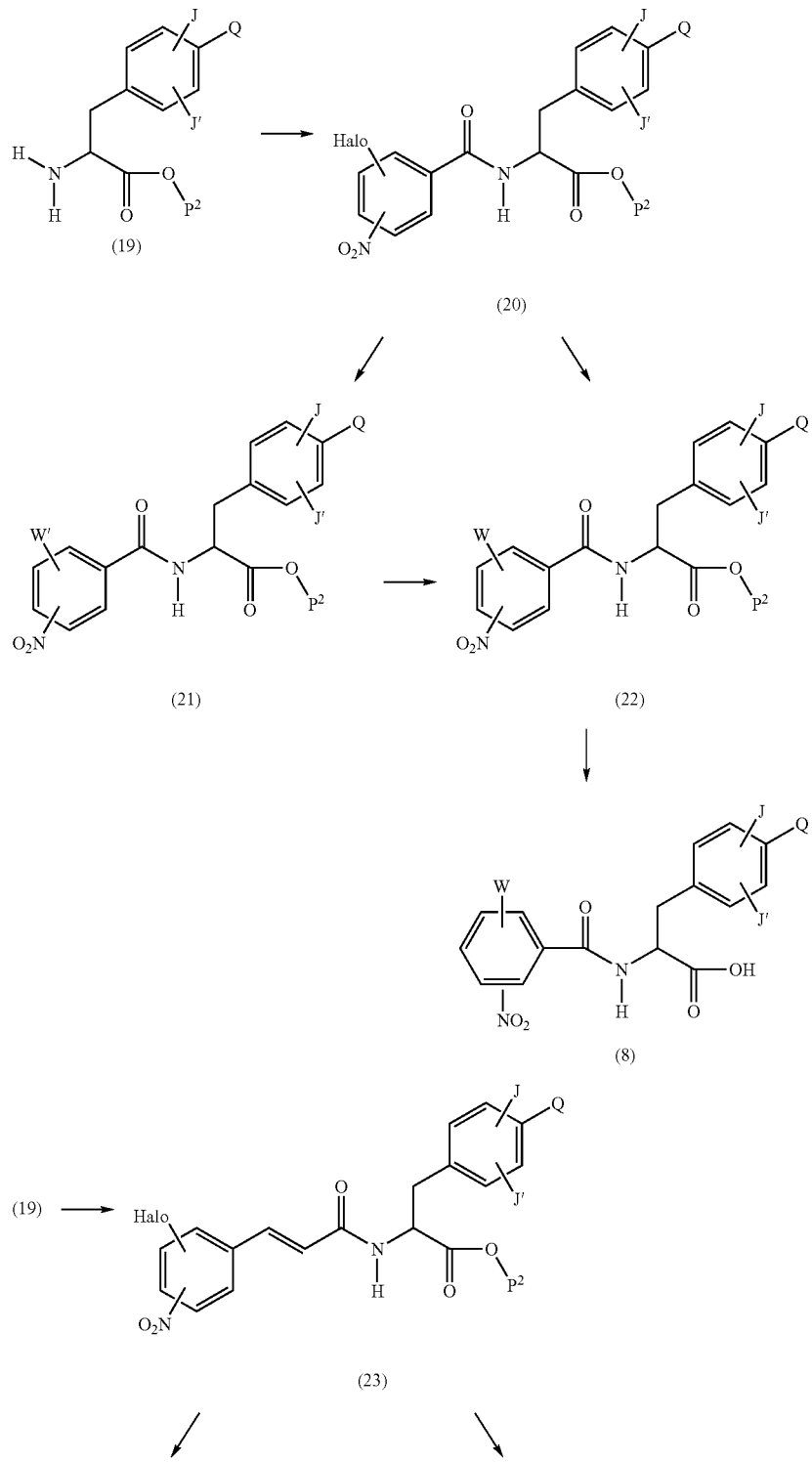

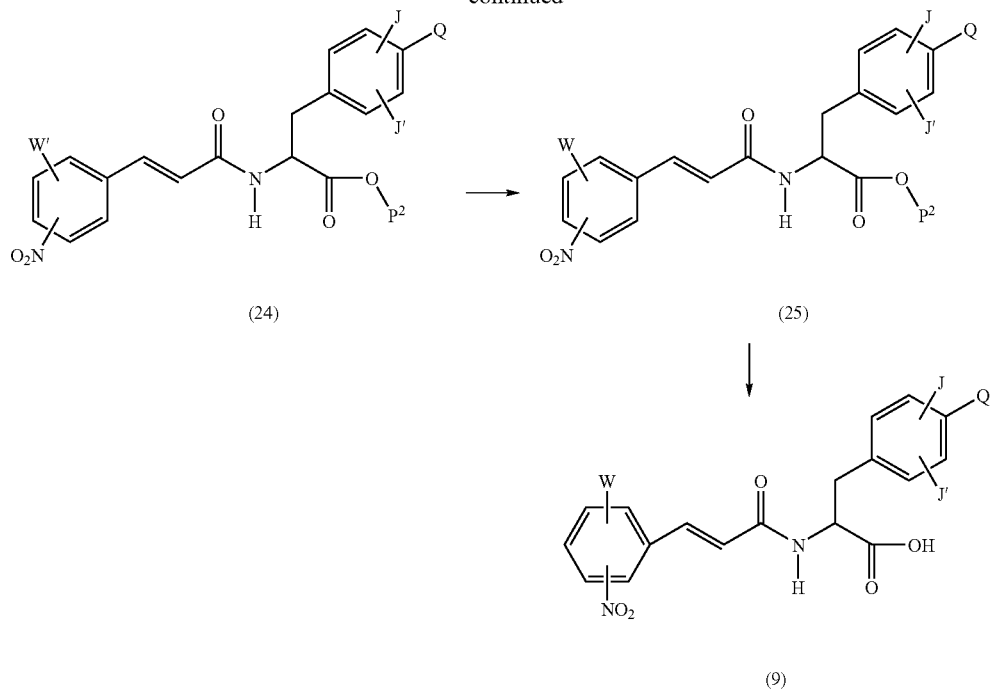

Namely, a suitably protected amine (19) is reacted with benzoic acid or cinnamic acid substituted with nitro group(s) and a halogen atom in the presence of, if necessary, a suitable additive such as HOAt or HOBt and a condensing agent such as DIC, DCC or EDC in an organic solvent such as dichloromethane, DMF or NMP to obtain an amide (20) or (23). The substituent Q of the amide (20) or (23) has a structure of —X-A as described above with reference to the general formula (1), or it is a substituent convertible into —X-A in any stage of the synthesis or the substituent which is suitably protected. The amide (20) or (23) can be converted into a phenylamine (22) or (25) by reacting it with the amine (6) or (7) in the presence of, if necessary a suitable additive such as triethylamine or diisopropylethylamine in an organic solvent such as DMF, DMSO or dichloromethane.

The phenylamine (22) or (25) can be obtained from the amide (20) or (23) through an amide (21) or (24). W' in the amide (21) or (24) represents a group which can be converted into W by removing the protective group in a subsequent step. The conversion of the amide (20) or (23) into the amide (21) or (24) is conducted under the same conditions as those in the conversion of the amide (13) or (15) into the phenylamine (16) or (18). The obtained amide (21) or (24) can be converted into the phenylamine (22) or (25) by removing the protective group.

The obtained phenylamine (22) or (25) can be converted into the carboxylic acid (8) or (9) by removing the protective group under suitable conditions. For example, when $P^2$ is methyl or ethyl group, the ester is hydrolyzed with an alkali; when $P^2$ is t-butyl group, the ester is treated with an acidic solution; and when $P^2$ is benzyl group or the like, the ester is hydrolyzed and reacted with hydrogen in the presence of a metallic catalyst to remove the protective group.

Phenylalanine derivatives (26) of general formula (1) wherein —X-A is a group defined in Q as described above, Y is a group of the formula: —SO$_2$—, Z is phenyl group, B is hydroxyl group, C is hydrogen atom, D is nitro group, E and F are each hydrogen atom and W is an amine derivative (3) or (4) are produced as follows:

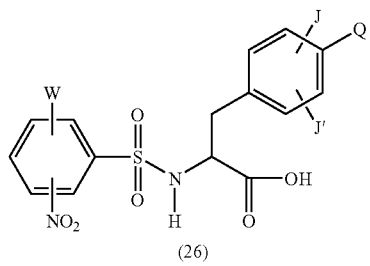

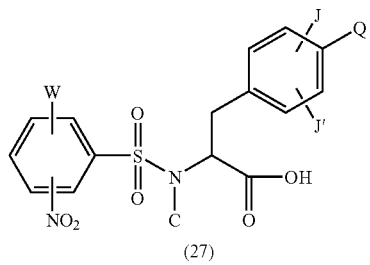

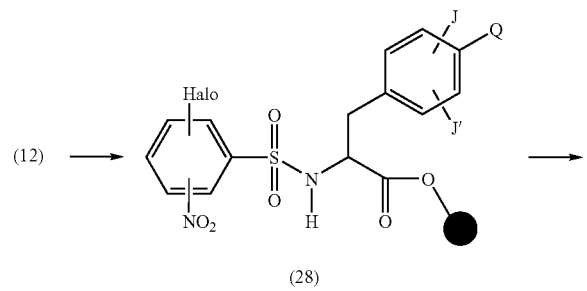

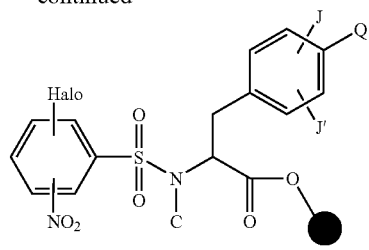

(29)

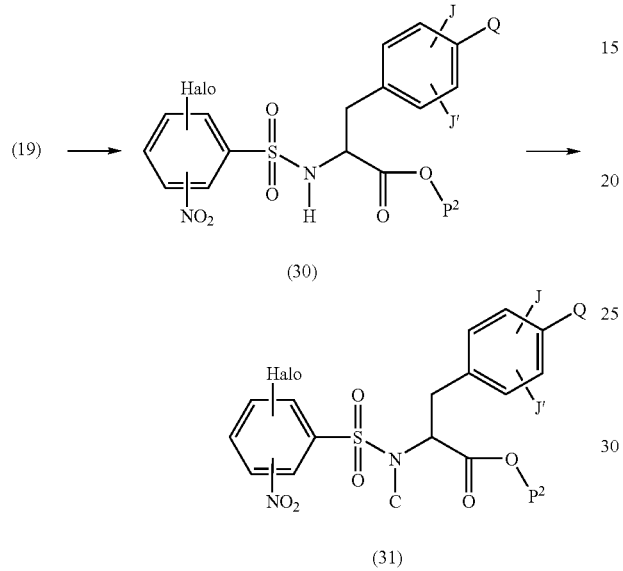

(19) → (30)

(31)

The amine (12) or (19) is reacted with a benzenesulfonyl chloride substituted with nitro group(s) and a halogen atom in the presence of, if necessary, a suitable additive such as pyridine or lutidine in an organic solvent such as dichloromethane, DMF or NMP to obtain a sulfonamide (28) or (30). The phenylalanine derivative (26) can be obtained by treating the sulfonamide (28) or (30) in the same manner as that in the synthesis of the carboxylic acid (8) or (9).

Phenylalanine derivatives (27) of general formula (1) wherein —X-A is a group as defined in Q as described above, Y is a group of the formula: —SO$_2$—, Z is phenyl group, B is hydroxyl group, C is a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D is nitro group, E and F are each hydrogen atom and W is an amine derivative (3) or (4) are produced as described below.

The sulfonamide (28) or (30) can be reacted with a suitable halide compound in the presence of an organic base such as triethylamine, diisopropylethylamine, pyridine or N,N-dimethylaminopyridine or an inorganic base such as potassium carbonate or sodium carbonate in an organic solvent such as DMF or dichloromethane to obtain a sulfonamide (29) or (31). The sulfonamide (29) or (31) can be synthesized also by Fukuyama—MITSUNOBU reaction with a suitable alcohol and the sulfonamide (28) or (30). The phenylalanine derivative (27) can be obtained also by treating the sulfonamide (29) or (31) in the same manner as that in the synthesis of the carboxylic acid (8) or (9).

Phenylalanine derivatives (32) or (33) of general formula (1) wherein —X-A is a group as defined in Q as described above, Y is a group of the formula: —NH—C(=O)— or NH—C(=S)—, Z is phenyl group, B is hydroxyl group, C is hydrogen atom, D is nitro group, E and F are each hydrogen atom and W is an amine derivative (3) or (4) are produced as follows:

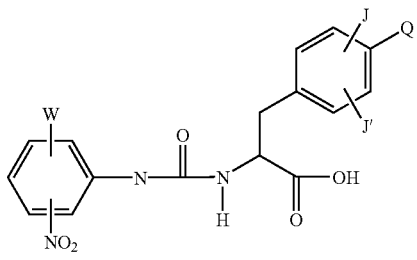

(32)

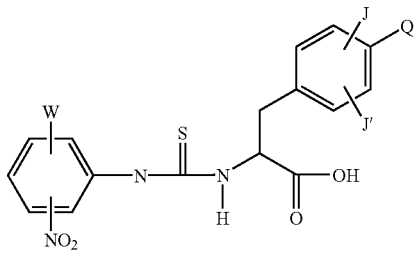

(33)

(12) → 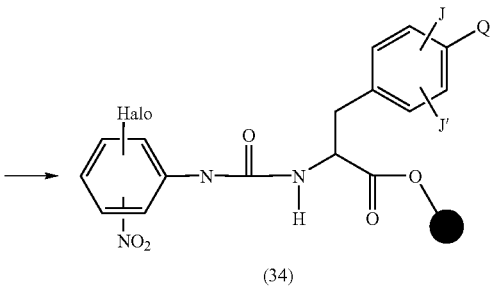

(34)

(19) → 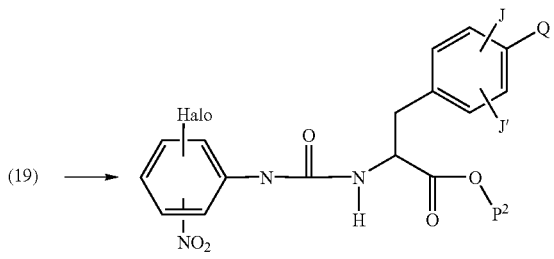

(35)

(12) → 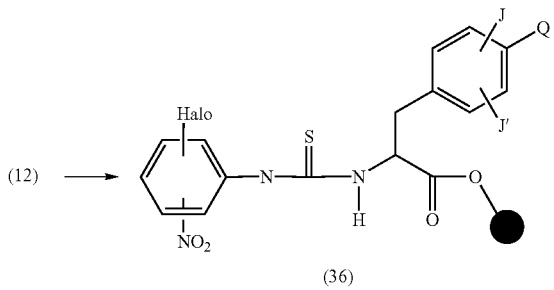

(36)

-continued

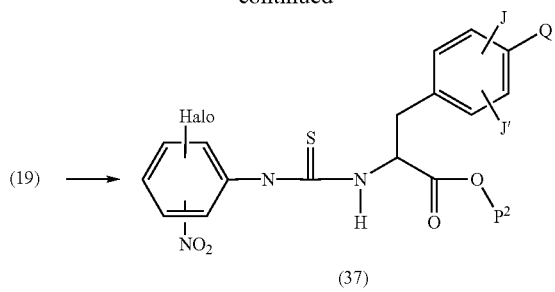

(37)

The amine (12) or (19) is reacted with an isocyanate or an isothiocyanate substituted with nitro group and a halogen atom in the presence of, if necessary, a suitable additive such as triethylamine or diisopropylethylamine in an organic solvent such as dichloromethane, DMF or NMP to obtain a urea (34) or (35) or thiourea (36) or (37). The phenylalanine derivative (32) or (33) can be obtained by treating the urea (34) or (35) or thiourea (36) or (37) in the same manner as that in the synthesis of the carboxylic acid (8) or (9).

Various partial structures of —X-A in the general formula (1) can be synthesized from corresponding precursors by reactions described below. By the reactions described below, Q in the precursor structure can be converted into —X-A in a suitable stage in an ordinary method for synthesizing the compounds of the general formula (1).

When Q is hydroxyl group or a suitably protected hydroxyl group, the protective group is removed, if necessary, to form hydroxyl group and then the subsequent conversion reaction can be conducted.

Hydroxyl group Q can be reacted with an alkylating agent such as an alkyl halide or an alkyl sulfonate in the presence of a suitable base in an organic solvent to form various ether-type structures. The ether-type compounds can be formed also by subjecting the obtained compound to Mitsunobu reaction with an alcohol in the presence of a dialkylazodicarboxylic acid. The compounds having structures of various aryl ether types or heteroaryl ether types can be formed by reacting the obtained compound with an aryl halide or a heteroaryl halide, in the presence of a suitable base or catalyst in an organic solvent.

Hydroxyl group Q can be reacted with a sulfonic acid halide or sulfonic acid anhydride in the presence of an organic base such as triethylamine, diisopropylethylamine, pyridine or N,N-dimethylaminopyridine or an inorganic base such as potassium carbonate or sodium carbonate in an organic solvent such as DMF or dichloromethane to form a corresponding product having a sulfonic acid ester type structure.

When Q is a properly protected amino group, the protective group can be removed to form the amino group by a method suitably selected depending on the protective group. When Q is nitro group, it can be converted into the amino group by the hydrogenation reaction in the presence of a metal catalyst or by the reduction reaction with a reducing agent selected from among various reducing agents. The amino group thus obtained can be further converted into groups of various structures by various reactions described below.

The amino group can be further converted into an alkylamino group by reacting it with an alkylating agent such as an alkyl halide or an alkyl sulfonate in the presence of a suitable base in an organic solvent. Various arylamine structures can be formed by reacting the amino group with an aryl halide in the presence of a suitable base in an organic solvent.

The amino group can be converted into an alkylamino group by reacting it with an aldehyde or a ketone in the presence of a reducing agent such as sodium borohydride or sodium cyanoborohydride in a solvent such as DMF, dichloromethane, a trialkylorthoformic acid or a trialkylorthoacetic acid. The amino group or alkylamino group can be converted into groups of various structures by reactions described below.

The amino group or alkylamino group can be converted into a corresponding structure of amide type or sulfonamide type by reacting it with a carboxylic acid halide, a carboxylic acid anhydride, a sulfonic acid halide or a sulfonic acid anhydride in the presence of an organic base such as triethylamine, diisopropylethylamine, pyridine or N,N-dimethylaminopyridine or an inorganic base such as potassium carbonate or sodium carbonate in an organic solvent such as DMF or dichloromethane. The amino group or alkylamino group can be converted into a corresponding structure of amide type also by reacting it with a carboxylic acid in the presence of a suitable additive and condensing agent in an organic solvent such as DMF or dichloromethane.

The amino group or alkylamino group can be converted into a corresponding structure of urea type or thiourea type by reacting it with an isocyanate or an isothiocyanate in the presence of, if necessary, an organic base such as triethylamine, diisopropylethylamine, pyridine or N,N-dimethylaminopyridine in an organic solvent such as DMF, toluene or dichloromethane.

The product having the sulfonamide structure formed as described above can be alkylated by the above-described Mitsunobu reaction with an alcohol. The alkylation reaction can be carried out also by reacting the compound with an alkylating agent such as an alkyl halide or an alkyl sulfonate in the presence of a suitable base in an organic solvent.

The formation of optical isomers of the phenylalanine derivatives represented by the general formula (1) in the present invention is possible because they have an asymmetric carbon atom. The compounds of the present invention also include those optical isomers. Various tautomers of the phenylalanine derivatives of the general formula (1) are possible in the present invention because they contain Free hydrogen atoms. The compounds of the present invention also include those tautomers. When the compounds of general formula (1) can form salts thereof, the salts must be pharmaceutically acceptable ones. When the compound has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group, the salts can be those with inorganic acids, e.g. hydrochloric acid, sulfuric acid and phosphoric acid; those with organic carboxylic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersing agent or by the cation exchange or anion exchange reaction when the salt is in the form of another salt.

The compounds of the general formula (1) of the present invention include also solvates thereof such as hydrates and alcohol adducts thereof.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets, depots and syrups. They can be prepared with ordinary preparation assistants by an ordinary method. The medicinal compositions preferably contain a pharmaceutically acceptable carrier and/or diluent in addition to the compound of general formula (1) or a salt thereof.

For example, the tablets are prepared by mixing the phenylalanine derivative, the active ingredient of the present invention, with additives selected from among known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, Akamono (Gaultheria adenothrix)oil and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, inverted sugars, glucose and vegetable oils.

The antagonist containing one of the compounds of above general formula (1) or one of salts thereof as active ingredient is usable as a therapeutic agent or preventing agent for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

The dose of the compound of general formula (1) or salt thereof used for the above-described purpose varies depending on the intended therapeutic effect, administration method, period of the treatment, and age and body weight of the patient. The dose is usually 1 µg to 5 g a day for adults in the oral administration, and 0.01 µg to 1 g a day for adults in the parenteral administration.

The following Examples will further illustrate the present invention, which are only preferred embodiments of the invention and which by no means limit the invention.

EXAMPLE 1

Preparation of Resin:

1.3 g of Wang resin (0.89 mmol/g) was suspended in NMP, and the obtained suspension was left to stand at room temperature for 3 hours. NMP was removed, and a solution of 2.0 g of N-(9-fluorenylmethoxycarbonyl)-O-(2,6-dichlorobenzyl)-L-tyrosine, 0.74 ml of diisopropyl carbodiimide (DIC) and 36 mg of dimethylaminopyridine in 30 ml of NMP was added to the resin. The resultant mixture was stirred at room temperature for 20 hours. The superfluous solvent was removed, and the resin was washed with 30 ml of NMP and 30 ml of dichloromethane twice each. The obtained resin was treated with 20% solution of piperidine in DMF at room temperature for 3 hours. The solvent was removed, and the residue was washed with 30 ml of each of DMF and dichloromethane 3 times. The obtained resin was used for the subsequent reaction.

EXAMPLE 2

Synthesis of N-(3-(N-isopropylaminoethyl-N'-isopropyl)amino-6-nitrobenzoyl)-O-(2,6-dichloro benzyl)tyrosine:

The resin obtained in Example 1 was added to a solution of 878 mg of 5-fluoro-2-nitrobenzoic acid, 969 mg of HOAt, 939 µl of DIC and 30 ml of NMP to conduct the reaction at room temperature for 20 hours. The reaction solution was removed, and the resin was washed with 30 ml of NMP and 30 ml of dichloromethane 3 times each. 5 ml of DMSO, 200 µl of diisopropylethylamine and 500 µl of N,N'-diisopropylethylenediamine were added to 20 mg of the resin and the reaction was conducted at 60° C. for 3 days. The reaction solution was removed and the resin was washed with DMSO, DMF and dichloromethane 3 times each. The resin was treated with 500 µl of trifluoroacetic acid/water (95/5) for 1 hour. The resin was taken by the filtration and further washed with trifluoroacetic acid. The wash solutions were combined together, concentrated and purified by the reversed-phase HPLC (ODS column, developer: water (containing 0.05% of TFA) and acetonitrile (containing 0.05% of TFA)) to obtain 3.0 mg of the intended compound.

The structure and MS (ESI+) (actual measurements) are also shown in Table 1.

MS (ESI+): 631, 633, 635

$[C_{31}H_{36}Cl_2N_4O_6$: 630, 632, 634]

EXAMPLES 3 TO 23

Compounds were synthesized by reacting the resin prepared in Example 1 with a corresponding amine in the same manner as that of Example 2.

The structures and MS (ESI+) are shown in Tables 1 to 5.

EXAMPLE 24

The resin obtained in Example 1 was condensed with 2-fluoro-5-nitrobenzoic acid in the same manner as that of Example 2. The reaction solution was removed, and the resin was washed with 30 ml of NMP and 30 ml of dichloromethane 3 times each. A DMSO solution comprising 5 ml of DMSO, 200 µl of diisopropylethylamine and 500µl of diethylamine was added to 100 mg of the resin, and the reaction was conducted at 60° C. for 3 days. The reaction solution was removed and the resin was washed with DMSO, DMF and dichloromethane 3 times each. The obtained resin was dried. 3 ml of a solution prepared from stannic chloride dihydrate (15.0 g), NMP (30 ml)·dihydrate and NMP (30 ml)·EtOH (1.5 ml) was added to the resin, and the reaction was conducted at room temperature for 16 hours. The reaction solution was removed and the resin was washed with NMP and dichloromethane 3 times each and then dried under reduced pressure. 50 mg of the obtained resin was added to a solution of 170 mg of Fmoc-N-methylglycine, 140 mg of HOAt, 150 µl of DIC and 5 ml of DMF to conduct the reaction at room temperature for 20 hours. 20% solution (25 ml) of piperidine in NMP was added to the reaction mixture to conduct the reaction for 10 minutes. The solvent was removed, and the residue was washed with NMP and dichloromethane 3 times each and then dried under reduced pressure.

The resin thus obtained was immersed in 100% trifluoroacetic acid for 1 hour. The resin was taken by the filtration and washed with trifluoroacetic acid. The wash solutions were combined together, concentrated and purified by the reversed-phase HPLC (ODS column, developer: water (containing 0.05% of TFA) and acetonitrile (containing 0.05% of TFA)) to obtain the intended compound. The structure and MS (ESI+) are shown in Table 5.

TABLE 1

| Ex. | Structure | MS(ESI+) [M + H]+ actual measurement |
|---|---|---|
| 2 | 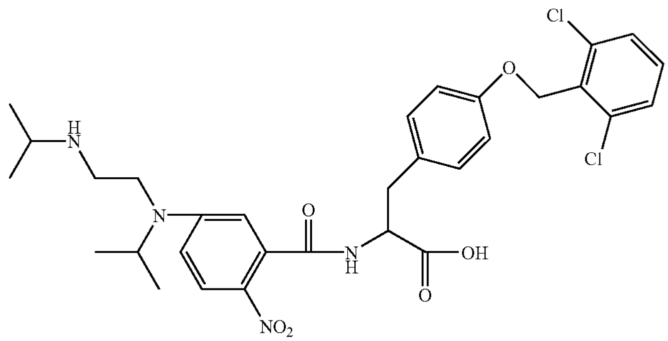 | 631, 633, 635 |
| 3 | 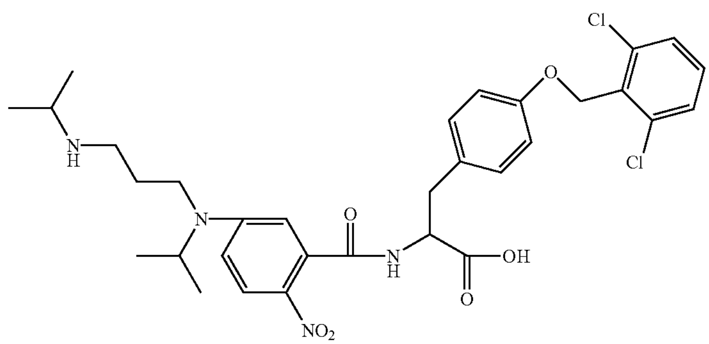 | 645, 647, 649 |
| 4 | 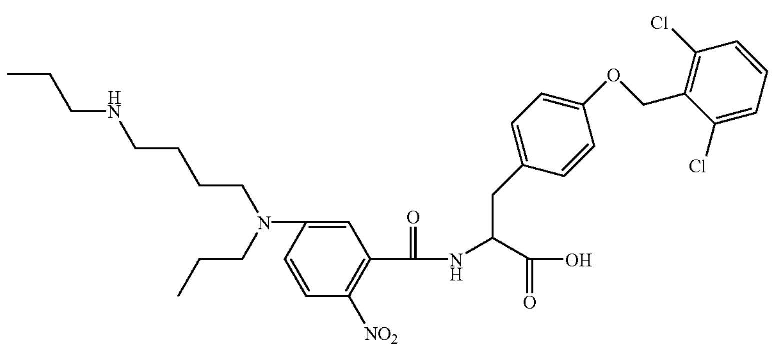 | 659, 661, 663 |
| 5 | 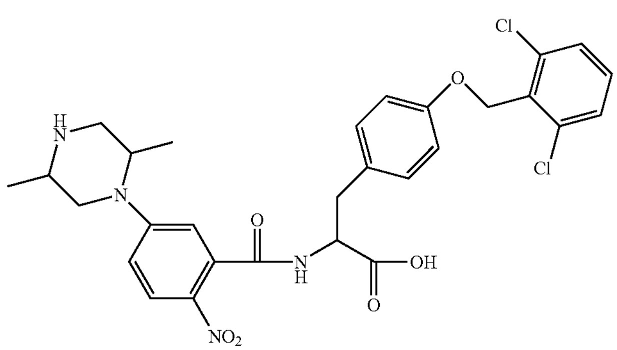 | 601, 603, 605 |

TABLE 1-continued

| Ex. | Structure | MS(ESI+) [M + H]+ actual measurement |
|---|---|---|
| 6 | (structure) | 629, 631, 633 |

TABLE 2

| Ex. | Structure | MS(ESI+) [M + H]+ actual measurement |
|---|---|---|
| 7 | (structure) | 603, 605, 607 |
| 8 | (structure) | 573, 575, 577 |
| 9 | (structure) | 574, 576, 578 |

TABLE 2-continued
| Ex. | Structure | MS(ESI+) [M + H]+ actual measurement |
|---|---|---|
| 10 | 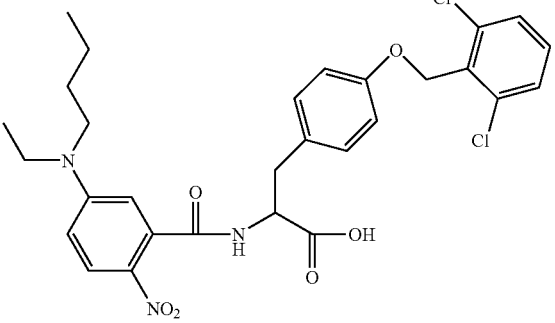 | 588, 590, 592 |
| 11 | 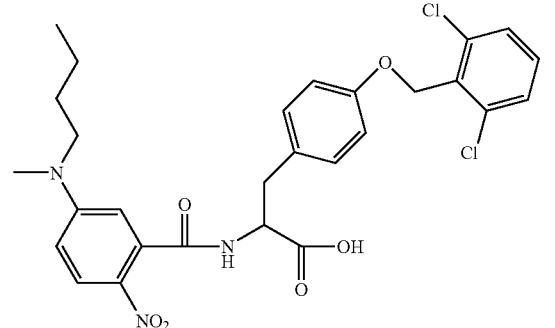 | 604, 606, 608 |
TABLE 3
| Ex. | Structure | MS(ESI+) [M + H]+ actual measurement |
|---|---|---|
| 12 | 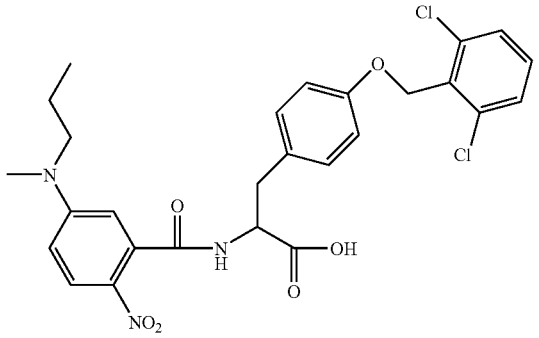 | 560, 562, 564 |
| 13 | 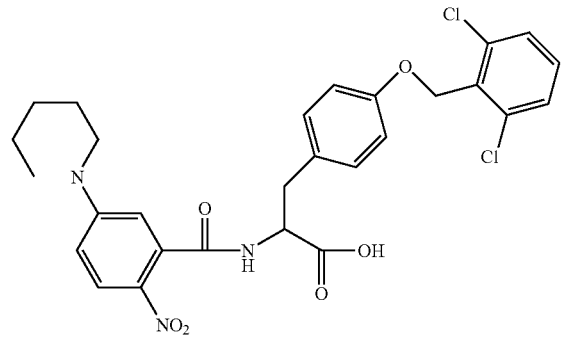 | 572, 574, 576 |

TABLE 3-continued
| Ex. | Structure | MS(ESI+) [M + H]+ actual measurement |
|---|---|---|
| 14 | 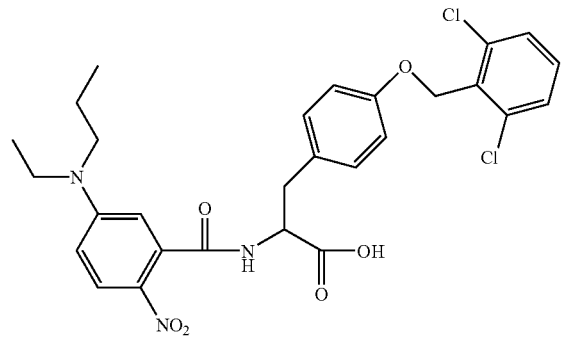 | 588, 590, 592 |
| 15 | 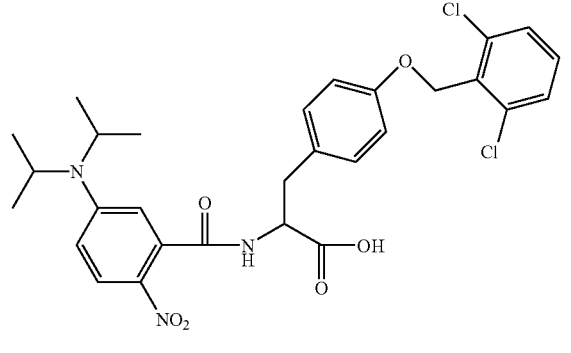 | 574, 576, 578 |
| 16 | 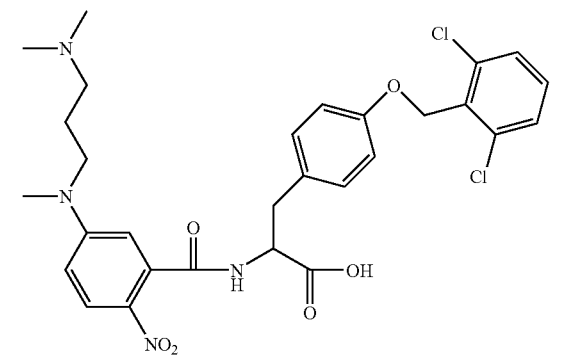 | 603, 605, 607 |

TABLE 4

| Ex. | Structure | MS(ESI+) [M + H]+ actual measurement |
|---|---|---|
| 17 | 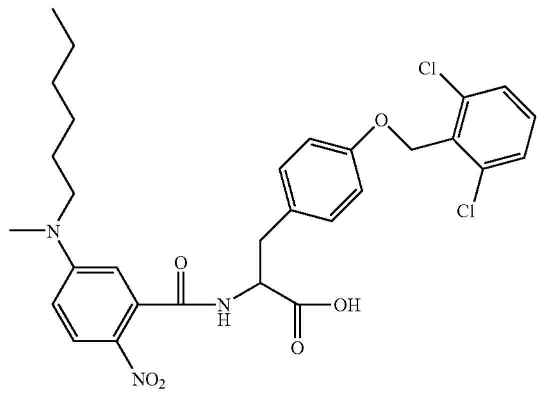 | 602, 604, 606 |
| 18 | 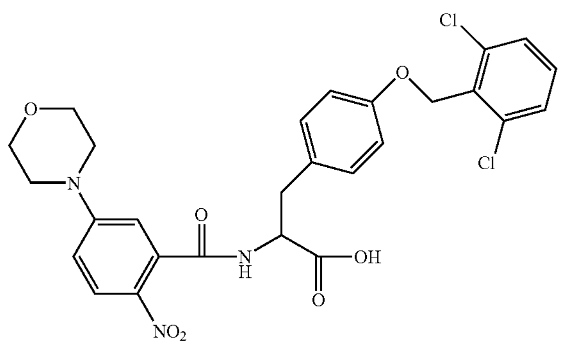 | 574, 576 |
| 19 | 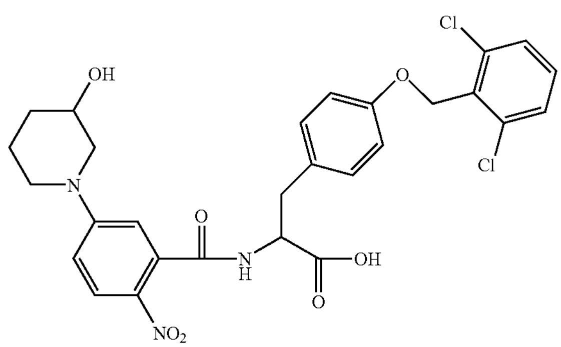 | 602, 604 |
| 20 | 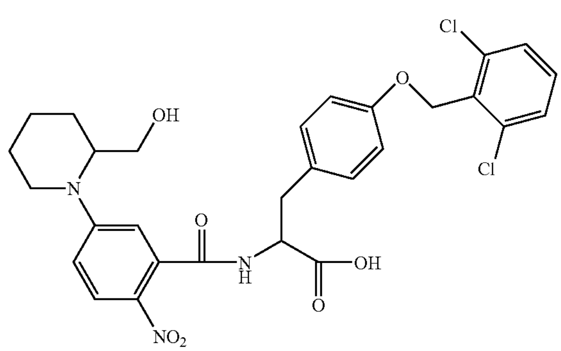 | 588, 590 |

TABLE 4-continued
| Ex. | Structure | MS(ESI+) [M + H]+ actual measurement |
|---|---|---|
| 21 | 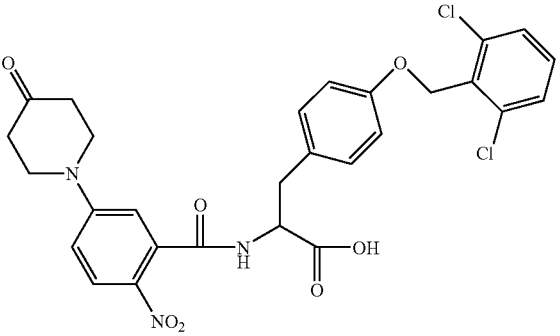 | 586, 588 |
TABLE 5
| Ex. | Structure | MS(ESI+) [M + H]+ actual measurement |
|---|---|---|
| 22 | 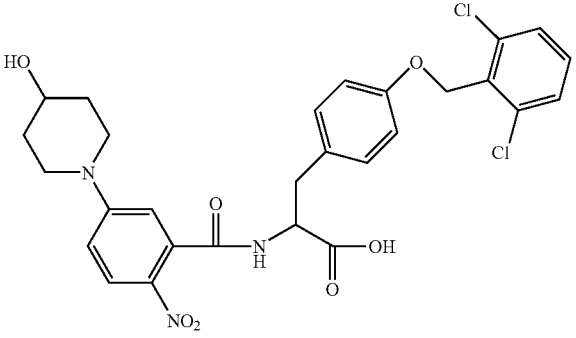 | 588, 590 |
| 23 | 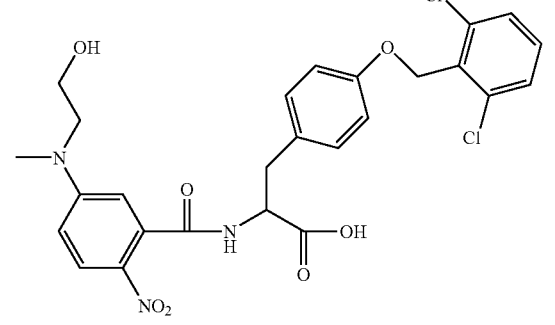 | 562, 564 |
| 24 | 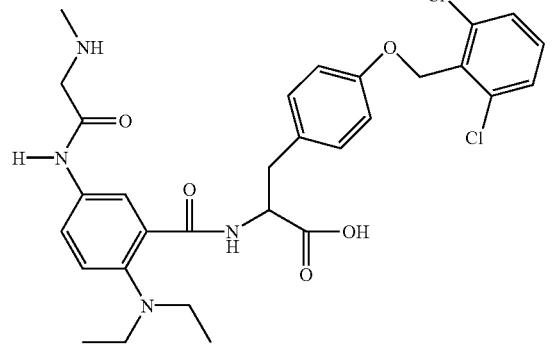 | 601, 603 |

EXAMPLE 25

The resin prepared in Example 1 was reacted with 4-fluoro-3-nitrobenzoic acid and piperazine in the same manner as that of Example 2 to obtain an intended compound.

The structure and MS (ESI+) are shown in Table 6.

TABLE 6

| Ex. | Structure | MS(ESI+) [M + H]+ actual measurement |
|---|---|---|
| 25 | (structure: piperazine–phenyl(NO2)–C(O)NH–CH(COOH)–CH2–phenyl–O–CH2–(2,6-dichlorophenyl)) | 573, 575, 577 |

EXAMPLE 26

Step 1 Preparation of Resin:

A solution of Fmoc-L-Phe(4-nitro)-OH (2.5 g), 2,6-dichlorobenzoyl chloride (0.745 ml) and pyridine (1.5 ml) in NMP (25 ml) was added to Wang resin (0.76 mmol/g, 2.3 g), and they were stirred at room temperature for 16 hours. The superfluous solvent was removed, and the resin was washed with DMF 3 times, with dichloromethane 3 times and with NMP twice. The resin was treated with acetic anhydride (20 ml), pyridine (20 ml) and NMP (20 ml) for 2 hours for capping unreacted hydroxyl group on the resin. The superfluous solvent was removed. The resin was washed with DMF and dichloromethane 3 times each and then dried under reduced pressure.

Step 2 Reduction of Nitro Group:

A solution of stannic chloride dihydrate (15.0 g) in NMP (30 ml)·EtOH (1.5 ml) was added to 1.5 g of the resin obtained in step 1 to conduct the reaction at room temperature for 16 hours. The reaction solution was removed, and the resin was washed with NMP and dichloromethane 3 times each and then dried under reduced pressure.

Step 3 Acylation Reaction:

500 mg of the resin obtained in step 2 was added to a solution of 170 mg of 4-phenyl-1,2,3-thiadiazole-5-carboxylic acid, 140 mg of HOAt and 150 µl of DIC in 1.5 ml of DMF to conduct the reaction at room temperature for 20 hours. The reaction solution was removed. The resin was washed with DMF, dichloromethane and ether 3 times each and then dried under reduced pressure.

Step 4 Removal of Fmoc Group:

20% piperidine solution (25 ml) was added to the resin obtained in step 3 to conduct the reaction for 10 minutes. The solvent was removed. 20% solution (25 ml) of piperidine in NMP was added to the residue to conduct the reaction for 10 minutes. The solvent was removed, and the residue was washed with NMP and dichloromethane 3 times each and then dried under reduced pressure.

Step 5:

The resin obtained in step 4 was added to a solution of 878 mg of 5-fluoro-2-nitrobenzoic acid, 969 mg of HOAt and 939 µl of DIC in 30 ml of NMP to conduct the reaction at room temperature for 20 hours. The reaction solution was removed, and the resin was washed with 30 ml of NMP and 30 ml of dichloromethane 3 times each. 5 ml of DMSO, 200 µl of diisopropylethylamine and 500 µl of N,N'-diisopropylethylenediamine were added to 20 mg of the resin, and the reaction was conducted at 60° C. for 3 days. The reaction solution was removed, and the resin was washed with DMSO, DMF and dichloromethane 3 times each. The resin was treated with 500 µl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA)) to obtain 1.6 mg of the intended compound.

The structure and MS (ESI+) (actual measurements) are shown in Table 7.

EXAMPLE 27

The same procedure as that in step 3 in Example 26 was repeated except that 5-chloro-2-(methylthio)pyrimidine-4-carboxylic acid was used as the carboxylic acid to obtain 29.6 mg of the intended compound.

The structure and MS (ESI+) are shown in Table 7.

EXAMPLE 28

Step 1:

A solution of 5-fluoro-2-nitrobenzoic acid (2.5 g), 2,6-dichlorobenzoyl chloride (0.745 ml) and pyridine (1.5 ml) in NMP (25 ml) was added to Wang resin (0.76 mmol/g, 2.3 g), and they were stirred at room temperature for 16 hours. The superfluous solvent was removed, and the resin was washed with DMF 3 times, with dichloromethane 3 times and with NMP twice. The resin was treated with acetic anhydride (20 ml), pyridine (20 ml) and NMP (20 ml) for 2 hours for capping unreacted hydroxyl group on the resin. The superfluous solvent was removed. The resin was washed with DMF and dichloromethane 3 times each and then dried under reduced pressure.

Step 2:

50 ml of DMSO, 2 ml of diisopropylethylamine and 5 ml of N,N'-diisopropylethylenediamine were added to the resin obtained in step 1 to conduct the reaction at 60° C. for 3 days. The reaction solution was removed. The resin was washed with DMSO, DMF and dichloromethane 3 times each and then dried under reduced pressure. 5 g of Fmoc-succinimide and 25 ml of NMP were added to the obtained resin, and they were stirred at room temperature for 16 hours. The superfluous solvent was removed. The resin was washed with DMF 3 times, with dichloromethane 3 times, with NMP twice and again with dichloromethane 3 times, and then dried under reduced pressure. The resin thus obtained was treated with 500 μl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain a benzoic acid derivative having a partial structure in Example 28.

Step 3:

400 mg of the benzoic acid derivative obtained in step 2, 480 mg of HOAt, 460 μl of DIC and 15 ml of NMP were added to the resin free of phenylalanine N-terminal obtained in the course of the preparation in Example 27, and the reaction was conducted at room temperature for 20 hours. The reaction solution was removed, and the resin was washed with 30 ml of NMP ad 30 ml of dichloromethane 3 times each. The reaction solution was removed. The resin was washed with DMSO, DMF and dichloromethane 3 times each and then dried.

Step 4:

20% piperidine solution (25 ml) was added to the resin obtained in step 3 to conduct the reaction for 10 minutes. The solvent was removed. 20% solution of piperidine in NMP (25 ml) was added to the residue to conduct the reaction for 10 minutes. The solvent was removed, and the residue was washed with NMP and dichloromethane 3 times each, and then dried under reduced pressure. The resin thus obtained was treated with 500 μl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) (actual measurements) are shown in Table 7.

EXAMPLE 29

A part of the resin treated with piperidine in step 4 in Example 28 was taken. Acetic anhydride (2 ml), pyridine (1 ml) and NMP (5 ml) were added to the resin, and they were stirred for 2 hours. The superfluous solvent was removed, and the resin was washed with DMF and dichloromethane 3 times each and then dried under reduced pressure. After drying the resin, 3 ml of a solution of stannic chloride dihydrate (15.0 g) in NMP (30 ml)·EtOH (1.5 ml) was added to the resin to conduct the reaction at room temperature for 16 hours. The reaction solution was removed, and the resin was washed with NMP and dichloromethane 3 times each and then dried under reduced pressure. The resin thus obtained was treated with 500 μl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) are shown in Table 7.

TABLE 7

| Ex. | Structure | MS(ESI+)[M + H]+ actual measurement |
|---|---|---|
| 26 | 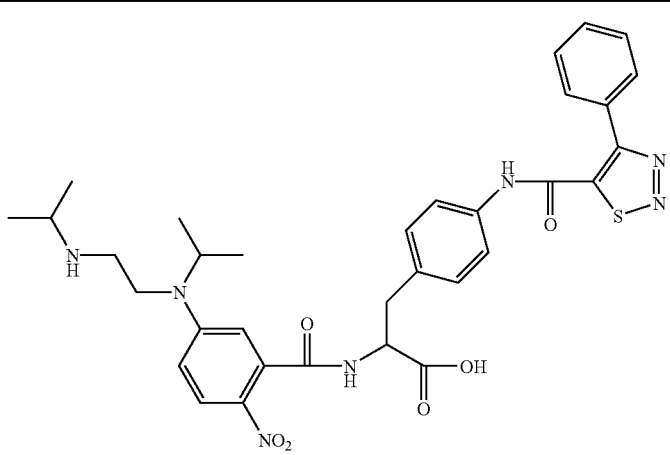 | 660 |

TABLE 7-continued

| Ex. | Structure | MS(ESI+)[M + H]+ actual measurement |
|---|---|---|
| 27 | 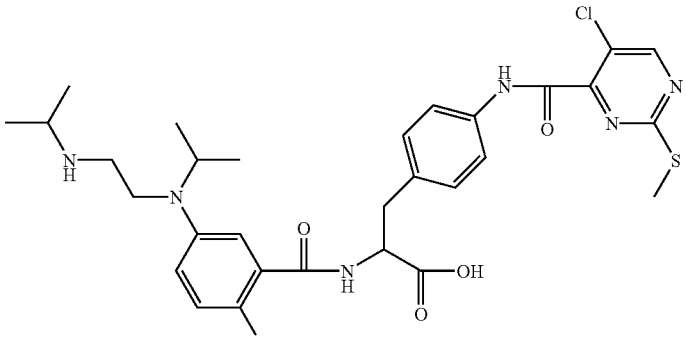 | 658, 660 |
| 28 | 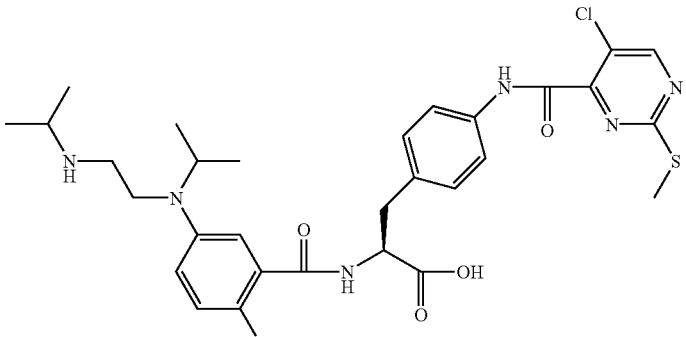 | 658, 660 |
| 29 | 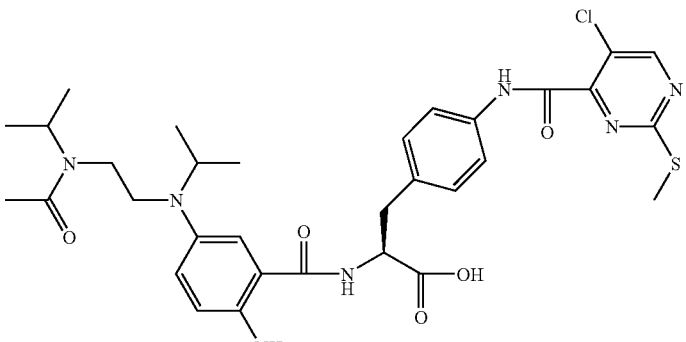 | 670, 672 |

EXAMPLE 30

A part of the resin treated with acetic anhydride in Example 29 and then dried was taken. The resin was treated with 500 μl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) are shown in Table 8.

EXAMPLE 31

A part of the resin just before the treatment with trifluoroacetic acid in Example 28 was taken. 3 ml of a solution of stannic chloride dihydrate (15.0 g) in NMP (30 ml)·EtOH (1.5 ml) was added to the resin to conduct the reaction at room temperature for 16 hours. The reaction solution was removed, and the resin was washed with NMP and dichloromethane 3 times each and then dried under reduced pressure. The resin thus obtained was treated with 500 µl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) are shown in Table 8.

EXAMPLE 32

A part of the resin just before the treatment with piperidine in Example 28 was taken. 3 ml of a solution of stannic chloride dihydrate (15.0 g) in NMP (30 ml)·EtOH (1.5 ml) was added to the resin to conduct the reaction at room temperature for 16 hours. The reaction solution was removed, and the resin was washed with NMP and dichloromethane 3 times each and then dried under reduced pressure. Acetic anhydride (2 ml), pyridine (1 ml) and NMP (5 ml) were added to the resin, and they were stirred for 2 hours. The superfluous solvent was removed, and the resin was washed with DMF and dichloromethane 3 times each and then dried under reduced pressure. 20% piperidine solution (25 ml) was added to the obtained resin to conduct the reaction for 10 minutes. The solvent was removed. 20% solution of piperidine in NMP (25 ml) was added to the residue and the reaction was conducted for 10 minutes. The solvent was removed, and the residue was washed with NMP and dichloromethane 3 times each and then dried under reduced pressure. The resin thus obtained was immersed in 500 µl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) are shown in Table 8.

EXAMPLE 33

A part of the resin just before the treatment with trifluoroacetic acid in Example 31 was taken. Acetic anhydride (2 ml), pyridine (1 ml) and NMP (5 ml) were added to the resin, and they were stirred for 2 hours. The superfluous solvent was removed, and the resin was washed with DMF and dichloromethane 3 times each and then dried under reduced pressure. The resin was immersed in 500 µl of trifluoroacetic acid/water (95/5) for 1 hour. The resin was taken by the filtration and then washed with trifluoroacetic acid. The wash solutions were combined together, concentrated and purified by the reversed-phase HPLC (ODS column, developer: water (containing 0.05% of TFA) and acetonitrile (containing 0.05% of TFA) to obtain the intended compound.

The structure and MS (ESI+) are shown in Table 8.

TABLE 8

| Ex. | Structure | MS(ESI+)[M + H]+ actual measurement |
|---|---|---|
| 30 | 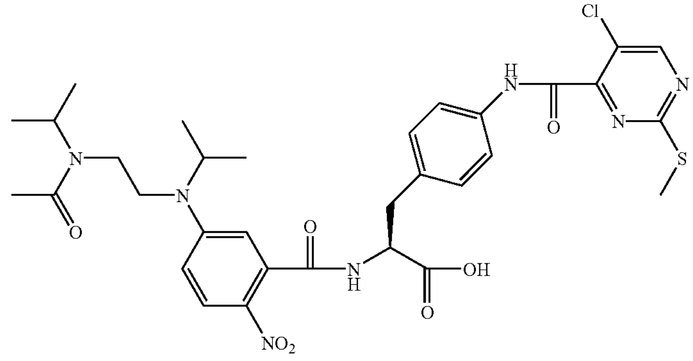 | 700, 702 |
| 31 | 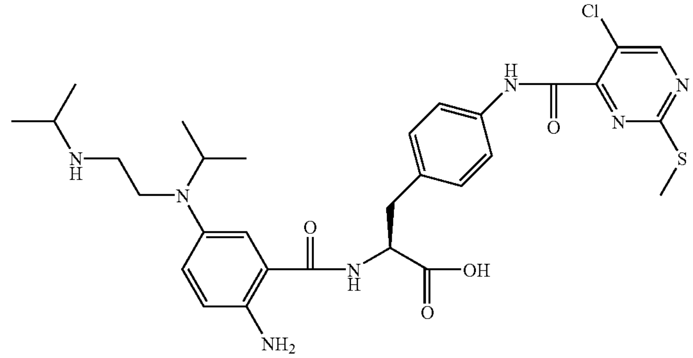 | 628, 630 |

TABLE 8-continued

| Ex. | Structure | MS(ESI+)[M + H]+ actual measurement |
|---|---|---|
| 32 | 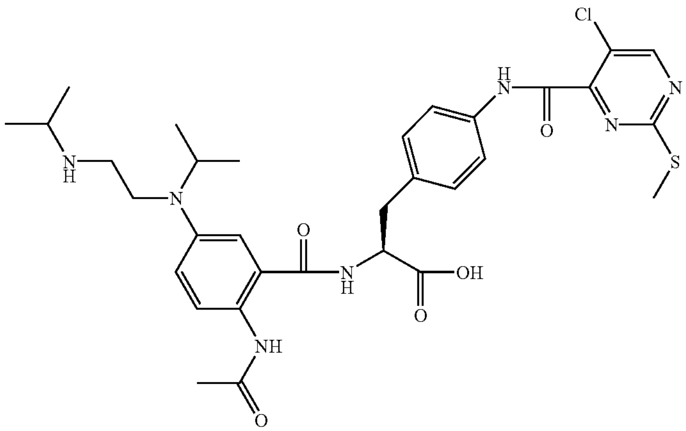 | 670, 672 |
| 33 | 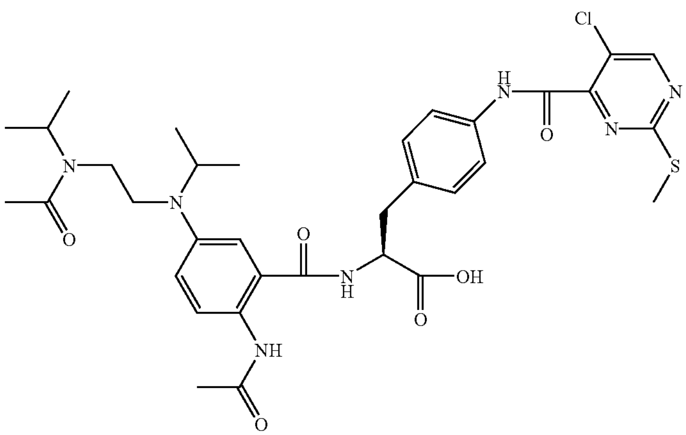 | 712, 714 |

(Test Example) VCAM Antagonistic Activity (VCAM-1/ α4β1 Binding Assay):

The capacity of a test substance antagonistic to the binding of cell strain Jurkat (ATCC TIB-152) of human T cells, known to express integrin α 4β1, to VCAM-1 was determined.

100 μl/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace® (Dainippon Pharmaceutical Co., Ltd.) with PBS to ¼ concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 μl of a test substance of various concentrations obtained by the dilution with the binding buffer was added to the plate. Immediately thereafter, 50 μl (final volume: 100 μl/well) of the fluorescent Jurkat cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

(Test Example) VCAM Antagonistic Activity (VCAM-1/ α4β7 Binding Assay):

The capacity of a test substance antagonistic to the binding of lymphoma cell strain RPMI-8866 of human B cells, known to express integrin α 4β7, to VCAM-1 was determined.

100 μl/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace® (Dainippon Pharmaceutical Co., Ltd.) with PBS to ¼ concentration was added in an amount of 150 μl/well. After the incubation at room temperature for 1 hour, buffer B was removed and the plate was washed with PBS once.

RPMI-8866 cells were incubated in DMEM containing 10 μg/ml of Calcein-AM (Wako Pure Chemical Industries, Ltd.) at 37° C. for 30 minutes to label with fluorescence. The cells were again suspended in a binding buffer (20 mM HEPES, DMEM containing 0.1% BSA) containing 4 mM of $MnCl_2$.

50 μl of a test substance of various concentrations obtained by the dilution with the binding buffer was added to the plate. Immediately thereafter, 50 μl (final volume: 100 μl/well) of the fluorescent RPMI-8866 cells ($4 \times 10^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

TABLE 9

| Ex. | VCAM-1/α 4 β 1 linking antagonization activity $IC_{50}$ (n mol/L) | VCAM-1/α 4 β 7 linking antagonization activity $IC_{50}$ (n mol/L) |
|---|---|---|
| 2 | 4000 | 100 |
| 3 | 5500 | 120 |
| 4 | 3700 | 120 |
| 5 | 4900 | 140 |
| 6 | 4800 | 150 |
| 7 | 9400 | 160 |
| 8 | 4000 | 750 |
| 11 | 3200 | 110 |
| 12 | 4100 | 360 |
| 13 | 19000 | 490 |
| 14 | 9300 | 890 |
| 18 | 2200 | 140 |
| 19 | 1900 | 300 |
| 20 | 2100 | 240 |
| 21 | 3300 | 160 |
| 22 | 4600 | 220 |
| 23 | 2200 | 66 |
| 25 | 4000 | 750 |
| 26 | 2400 | 37 |
| 27 | 27 | 1.2 |
| 28 | 23 | 1.1 |
| 30 | 87 | 5.3 |

It is thus apparent that the new phenylalanine derivatives exhibited an excellent α 4 integrin inhibiting activity.

Since the new phenylalanine derivatives of the present invention have excellent α 4 integrin inhibiting activity, the present invention provides a therapeutic agent or preventive agent for diseases in which α 4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

What is claimed is:

1. A phenylalanine compound of formula (1) or a pharmaceutically acceptable salt thereof:

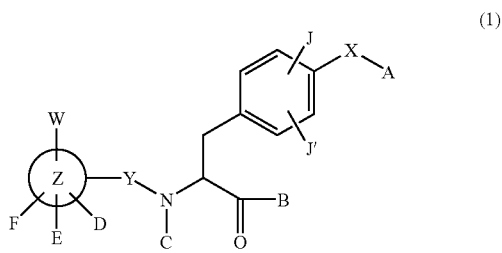

(1)

wherein X represents —NH—C(═O)—,
Y represents —C(═O)—, —C(═S)—, —SO$_2$—, —CH$_2$—(C═O)—, —NH—(C═O)—, NH—C (═S)— or —CH═CH—(C═O)—
Z represents, a phenyl group,
A represents a substituted pyrimidinyl group which is attached to X at the 6-position of said substituted pyrimidinyl group,
B represents a hydroxyl group,
C represents a hydrogen atom,
D, E and F may be the same or different from one another, and each represent a hydrogen atom, nitro group, a halogen atom, hydroxyl group, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a halogeno-lower alkanoyl group, a lower alkyloxy group, cyano group, a substituted or unsubstituted amino group, carboxyl group, a lower alkoxycarbonyl group, a substituted or unsubstituted carbamoyl group, a lower alkylthio group, a lower alkylsulfonyl group or a substituted or unsubstituted sulfamoyl group,
W represents a group of formula (3), (4) or (5):

(3)

(4)

-continued

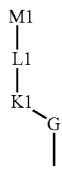

(5)

wherein:
G represents an oxygen atom, a sulfur atom, an interatomic bond, —C(=O)—, —C(=S)—, —SO$_2$—, or —S(=O)—,
$K^1$ and $K^2$ may be the same or different from each other, and each represent an interatomic bond, —C(=O)—, —C(=S)—, —SO$_2$—, or —S(=O)—,
$L^1$ and $L^2$ may be the same or different from each other, and each represent an interatomic bond, a lower alkyl group which may contain a hetero atom(s) in the chain thereof, a lower alkenyl group which may contain a hetero atom(s) in the chain thereof, a lower alkynyl group which may contain a hetero atom(s) in the chain thereof, a cycloalkyl group which may contain a hetero atom(s) in the ring thereof, an aryl group, a heteroaryl group or a hydroxy-lower alkyl group,
$M^1$ and $M^2$ may be the same or different from each other, and each represent a hydrogen atom, hydroxyl group, mercapto group, unsubstituted amino group, a monosubstituted amino group, a disubstituted amino group, carboxyl group, sulfo group, sulfino group, sulfeno group, a substituted or unsubstituted carbamoyl group, a substituted or unsubstituted sulfamoyl group, a lower alkyloxy group, a lower alkylthio group, a lower alkoxycarbonyl group, sulfonyl group, sulfinyl group, a halogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, a halogeno-lower alkanoyl group, an aroyl group, nitro group or cyano group,
P represents a substituted or unsubstituted lower alkyl group, a substituted or unsubstituted amino group, oxygen atom, sulfur atom, an interatomic bond, —C(=O)— or —CH(OH)—, and J and J' may be the same or different from each other and each represent a hydrogen atom, a halogen atom, a lower alkyl group, a lower alkyloxy group or nitro group.

2. The phenylalanine compound or pharmaceutically acceptable salt thereof according to claim 1, wherein W represents a group of formula (2) or (3),
$K^1$ and $K^2$ represent an interatomic bond, $L^1$ and $L^2$ may be the same or different from each other and they each represent a lower alkyl group which may contain a hetero atom(s) in the chain thereof or a lower alkenyl group which may contain a hetero atom(s) in the chain thereof, and
$M^1$ and $M^2$ may be the same or different from each other and they each represent a hydrogen atom, a hydroxyl group, an unsubstituted amino group, a monosubstituted amino group or a disubstituted amino group.

3. The phenylalanine and compound or pharmaceutically acceptable salt thereof according to claim 2, wherein D represents a nitro group.

4. The phenylalanine compound or pharmaceutically acceptable salt thereof according to claim 2, wherein
Y represents a group of the formula: —C(=O)—,
D represents a nitro group,
E and F each represent a hydrogen atom,
W represents a group of formula (3) or formula (4),
P represents a substituted or unsubstituted lower alkyl group or a substituted or unsubstituted amino group, and
J and J' each represent a hydrogen atom.

5. A pharmaceutical composition comprising a phenylalanine compound or a pharmaceutically acceptable salt thereof according to claim 1 and a pharmaceutically acceptable carrier.

6. The pharmaceutical composition of claim 5 wherein
Y represents a group of the formula: —C(=O)—,
D represents a nitro group,
E and F each represent a hydrogen atom,
W represents a group of formula (3) or formula (4),
$K^1$ and $K^2$ represent an interatomic bond,
$L^1$ and $L^2$ may be the same or different from each other and they each represent a lower alkyl group which may contain a hetero atom(s) in the chain thereof or a lower alkenyl group which may contain a hetero atom(s) in the chain thereof,
$M^1$ and $M^2$ may be the same or different from each other and they each represent a hydrogen atom, a hydroxyl group, an unsubstituted amino group, a monosubstituted amino group or a disubstituted amino group,
P represents a substituted or unsubstituted lower alkyl group or a substituted or unsubstituted amino group, and
J and J', each represent a hydrogen atom.

7. A pharmaceutical composition comprising a phenylalanine compound or a pharmaceutically acceptable salt thereof according to claim 2 and a pharmaceutically acceptable carrier.

8. A pharmaceutical composition comprising a phenylalanine compound or a pharmaceutically acceptable salt thereof according to claim 3 and a pharmaceutically acceptable carrier.

* * * * *